United States Patent
Ogai et al.

(10) Patent No.: US 12,370,326 B2
(45) Date of Patent: Jul. 29, 2025

(54) INJECTION NEEDLE

(71) Applicant: ASTI CORPORATION, Hamamatsu (JP)

(72) Inventors: Noriyuki Ogai, Hamamatsu (JP); Akinori Inoh, Hamamatsu (JP); Isamu Nonaka, Hamamatsu (JP)

(73) Assignee: ASTI CORPORATION, Hamamatsu (JP)

( * ) Notice: Subject to any disclaimer, the term of this patent is extended or adjusted under 35 U.S.C. 154(b) by 462 days.

(21) Appl. No.: 17/431,954

(22) PCT Filed: Feb. 24, 2020

(86) PCT No.: PCT/JP2020/007272
§ 371 (c)(1),
(2) Date: Aug. 18, 2021

(87) PCT Pub. No.: WO2020/175412
PCT Pub. Date: Sep. 3, 2020

(65) Prior Publication Data
US 2022/0152316 A1    May 19, 2022

(30) Foreign Application Priority Data
Feb. 25, 2019   (JP) .................................. 2019-031144

(51) Int. Cl.
*A61M 5/32*     (2006.01)
*A61M 5/158*    (2006.01)

(52) U.S. Cl.
CPC .......... *A61M 5/3298* (2013.01); *A61M 5/158* (2013.01)

(58) Field of Classification Search
CPC ... A61M 5/3298; A61M 5/3295; A61M 37/00
See application file for complete search history.

(56) References Cited

U.S. PATENT DOCUMENTS 3,814,097 A * 6/1974 Ganderton ........ A61M 37/0015
                                              600/556
3,964,482 A * 6/1976 Gerstel ............. A61M 37/0015
                                              604/890.1
(Continued)

FOREIGN PATENT DOCUMENTS

JP   2003-088584 A   3/2003
JP   2011-509735 A   3/2011
(Continued)

OTHER PUBLICATIONS

KR-20110013796-A, English Machine Translation, 2011 (Year: 2011).*

(Continued)

*Primary Examiner* — William R Carpenter
(74) *Attorney, Agent, or Firm* — HAUPTMAN HAM, LLP

(57) ABSTRACT

The purpose of the present invention is to provide an injection needle unit, provided with a plurality of needle pieces, with a simple structure and capable of easy manufacturing. The injection needle unit provided with: a needle base provided with a medicinal solution accommodation space; and a plurality of needle pieces, each of which is attached to the needle base, and a base end of the needle piece communicates to the medicinal solution accommodation space. The needle base is composed of: a needle base body, provided with an opening for opening the medicinal (Continued)

solution accommodation space in the direction orthogonal to the axis directions of the needle pieces; and a lid for enclosing the opening of the needle base body.

11 Claims, 19 Drawing Sheets

(56) References Cited

U.S. PATENT DOCUMENTS

| | | | | |
|---|---|---|---|---|
| 4,857,062 | A * | 8/1989 | Russell | A61M 39/0613 604/905 |
| 5,836,920 | A * | 11/1998 | Robertson | A61M 5/3216 604/263 |
| 8,172,815 | B2 | 5/2012 | Down et al. | |
| 10,744,311 | B2 | 8/2020 | Onozuka et al. | |
| 2010/0056989 | A1 * | 3/2010 | Mckay | A61B 17/3478 604/38 |
| 2010/0286618 | A1 * | 11/2010 | Choi | A61M 5/32 604/173 |
| 2013/0237925 | A1 * | 9/2013 | Trainer | A61M 25/0606 604/247 |
| 2014/0128810 | A1 | 5/2014 | Ozawa et al. | |
| 2020/0046957 | A1 | 2/2020 | Ogai et al. | |
| 2020/0188610 | A1 * | 6/2020 | Fretta | A61M 5/3293 |

FOREIGN PATENT DOCUMENTS

| | | | | |
|---|---|---|---|---|
| JP | 4836392 | B2 | 12/2011 | |
| JP | 2015-198786 | A | 11/2015 | |
| JP | 6068057 | B2 | 1/2017 | |
| JP | 2018-047227 | A | 3/2018 | |
| KR | 100902133 | B1 * | 6/2009 | |
| KR | 20110013796 | A * | 2/2011 | |
| WO | WO-2011073796 | A2 * | 6/2011 | A61M 5/19 |
| WO | WO-2012127856 | A1 * | 9/2012 | A61M 5/3298 |
| WO | WO-2013065235 | A1 * | 5/2013 | A61M 25/0084 |
| WO | 2015/115455 | A1 | 8/2015 | |
| WO | 2018/181639 | A1 | 10/2018 | |

OTHER PUBLICATIONS

KR-100902133-B1, English Machine Translation, 2009 (Year: 2009).*
WO-2013065235-A1, English Machine Translation, 2013 (Year: 2013).*
PCT/ISA/210, "International Search Report for International Application No. PCT/JP2020/007272," May 26, 2020.

* cited by examiner (a)

(b)

(a)

(b)

(a)

(b)

INJECTION NEEDLE

RELATED APPLICATIONS

The present application is National Phase of International Application No. PCT/JP2020/007272 filed Feb. 24, 2020, and claims priority from Japanese Application No. 2019-031144, filed Feb. 25, 2019, the disclosure of which is hereby incorporated by reference herein in its entirety.

TECHNICAL FIELD

The present invention relates to an injection needle unit, provided with a plurality of needle pieces, and in particular, relates to those having a simple structure and capable of easy manufacturing.

BACKGROUND ART

For example, intradermal or subcutaneous administrations of Botox (registered trade mark) or hyaluronic acid for the cosmetic purposes, intradermal or subcutaneous administrations of Botox (registered trademark) for the treatment of maschalephidrosis, and intradermal or subcutaneous administrations of steroid, PRP (platelet-rich plasma) or cells, etc., for the purpose of hair regeneration, are normally performed several times or even dozens of times in a single occasion of treatment. If such administrations are performed by using a single-needle type injection needle unit, the treatment will require much labor and a long period of time.

Thus, there has been a proposal of using of so-called "multiple needle unit," which is an injection needle unit provided with a plurality of injection needle pieces.

Patent Documents 1 to 4 disclose examples of this type of multiple needle unit.

First, a medicinal solution injection needle according to an invention as described in Patent Document 1 is composed of a medicinal solution injection needle body, and three needle pieces attached to the medicinal solution injection needle body. There is a space portion formed on the base end side of the medicinal solution injection needle body, into which a base end of the injection device is inserted.

Next, a multiple needle unit according to an invention as described in Patent Document 2 is provided with a needle hub, and the needle hub is composed of a first main body and a second main body. The first main body accommodates a plurality of needle pieces, and the second main body has a space portion formed therein, into which a tip of the injection device is inserted.

Next, an injection needle according to an invention as described in Patent Document 3 is composed of a needle base, a fit-in accommodation portion, a needle tube shield portion, etc., wherein, a plurality of needle pieces is attached to the needle base, and a space portion is formed on the side of the fit-in accommodation portion, and a tip of the injection device is inserted into the space portion.

Furthermore, a skin permeability enhancing device according to an invention as described in Patent Document 4 is provided with a support and a connecting member, and a plurality of cannulas is attached to the support, and a space portion is formed in the connection member, so that a tip of the injection device is inserted into the space portion.

REFERENCE DOCUMENTS OF CONVENTIONAL ART

Patent Document(s)

Patent Document 1: Official Gazette, Japan Patent No. 6068057.

Patent Document 2: Official Gazette, Japan Patent Publication No. 2011-509735A.

Patent Document 3: Official Gazette, Japan Patent Publication No. 2018-47227A.

Patent Document 2: Official Gazette, Japan Patent No. 4836392.

SUMMARY OF THE INVENTION

Problems to be Solved by Invention

However, the injection needles and injection devices according to the conventional art as described above have the following problem.

First, with regard to the invention as described in Patent Document 1, although the structure is simple because the medicinal solution injection needle body is composed of a single component, there has been a problem that the number of needle pieces and the needle pitch are limited.

For reference, where the increase of the number of needle pieces is attempted, the diameter of the portion of the medicinal solution injection needle body on the side of the needle pieces becomes relatively larger than the diameter of the portion of the medicinal solution injection needle body on the side of the injection device, and consequently, the shape of the medicinal solution injection needle body inevitably becomes complicated. In such a case, because of manufacturing issues (problems related to taking-out of a slide mold during molding process), it is expected that the accomplishment of a structure composed of a single component will become difficult.

Moreover, with regard to the invention as described in Patent Document 2, there has been a problem that the two components, i.e., the first main body and the second main body, are both relatively large and in complicated shapes.

Moreover, with regard to the invention a described in Patent Document 3, this invention is composed of a plurality of components, i.e., the needle base, the fit-in accommodation portion, the needle tube shield portion, etc., and consequently, the structure is complicated, and the manufacturing thereof is difficult.

And moreover, with regard to the invention as described in Patent Document 4, similar to the case of the invention as described above in Patent Document 2, there has been a problem that the two components, i.e., the support and the connecting member, are both relatively large and in complicated shapes, and consequently, the manufacturing thereof is difficult.

In the light of the above problem, it is an object of the present invention to provide an injection needle unit and an injection device, provided with a plurality of needle pieces, having a simple structure and capable of easy manufacturing.

Means to Solve the Problem

To achieve the objects mentioned above, according to a first aspect of the present invention, there is an injection needle unit provided with: a n needle base provided with a medicinal solution accommodation space; and a plurality of needle pieces, each of which is attached to the needle base, and a base end of the needle piece communicates to the medicinal solution accommodation space, wherein, the needle base is composed of a needle base body, provided with an opening for opening the medicinal solution accommodation space in the direction orthogonal to the axis directions of the needle pieces; and a lid for enclosing the opening of the needle base body.

Moreover, according to the injection needle unit of a second aspect of the present invention, with regard to the injection needle unit of the first aspect, the opening serves for taking-out of a slide mold for molding the medicinal solution accommodation space.

Moreover, according to the injection needle unit of a third aspect of the present invention, with regard to the injection needle unit according to the first or second aspect, the opening is provided on the side of the shorter length of the transverse section of the needle base body when looking down from above.

Moreover, according to the injection needle unit of a fourth aspect of the present invention, with regard to the injection needle unit according to any one of the first to third aspects, the needle base body has a recess formed therein, and the opening is provided at the bottom portion of the recess, and the recess is formed relatively larger than the opening.

Moreover, according to the injection needle unit of a fifth aspect of the present invention, with regard to the injection needle unit according to the fourth aspect, the lid is formed in a taper shape so that the size becomes thinner, from a base end portion to be engaged with the recess, toward a tip portion for enclosing the opening.

Moreover, according to the injection needle unit of a sixth aspect of the present invention, with regard to the injection needle unit according to any one the first to fifth aspects, the lid is a solidified sealing agent.

Moreover, according to the injection needle unit of a seventh aspect of the present invention, with regard to the injection needle unit according to the sixth aspect, the sealing agent is an adhesive.

Moreover, according to the injection needle unit of an eighth aspect of the present invention, with regard to the injection needle unit according to any one of the first to fifth aspects, the needle base body and the lid have been formed integrally in advance.

Moreover, according to the injection needle unit of a ninth aspect of the present invention, with regard to the injection needle unit according to any one of the first to eighth aspects, the plurality of needle pieces is configured so as to form multiple rows in the longitudinal direction/a single row in the lateral direction.

Moreover, according to the injection needle unit of a tenth aspect of the present invention, with regard to the injection needle unit according to any one of the first to eighth aspects, the plurality of needle pieces is configured so as to form multiple rows in the longitudinal direction/multiple rows in the lateral direction.

Moreover, according to the injection needle unit of an eleventh aspect of the present invention, with regard to the injection needle unit according to any one of the first to tenth aspects, a tip of each of the plurality of needle pieces has been formed as a slant edge surface, and the oriented direction of each of the slant edge surface is irregularly arranged.

Moreover, according to the injection needle unit of a twelfth aspect of the present invention, with regard to the injection needle unit according to any one the first to tenth aspects, a tip of each of the plurality of needle pieces has been formed as a slant edge surface, and the oriented direction of the slant edge surface of each of the plurality of needle pieces is regularly arranged.

Moreover, according to the injection needle unit of a thirteenth aspect of the present invention, with regard to the injection needle unit according to the twelfth aspect, the slant edge surfaces of all of the plurality of needle pieces are oriented in the same direction.

Moreover, according to the injection needle unit of a fourteenth aspect of the present invention, with regard to the injection needle unit according to the twelfth aspect, the plurality of needle pieces is configured so as to form multiple rows in the longitudinal direction/multiple rows in the lateral direction, and the slant edge surfaces of the needle pieces other than the center needle piece are oriented inwardly in the radial direction or outwardly in the radial direction.

And moreover, an injection device of a fifteenth aspect of the present invention is provided with: a syringe; and the injection needle unit according to any one of the first to fourteenth aspects, attached to a tip of the syringe.

Effect of the Invention

As described above, according to the first aspect of the present invention, there is an injection needle unit provided with: a n needle base provided with a medicinal solution accommodation space; and a plurality of needle pieces, each of which is attached to the needle base, and a base end of the needle piece communicates to the medicinal solution accommodation space, wherein, the needle base is composed of a needle base body, provided with an opening for opening the medicinal solution accommodation space in the direction orthogonal to the axis directions of the needle pieces; and a lid for enclosing the opening of the needle base body. Therefore, the injection needle unit is provided with a plurality of needle pieces with a simple structure, which can be manufactured easily.

Moreover, according to the injection needle unit of the second aspect of the present invention, with regard to the injection needle unit according to the first aspect, the opening serves for taking-out of a slide mold for molding the medicinal solution accommodation space. Therefore, the taking-out of the slide mold can be performed securely, and the above effect can be accomplished more securely.

Moreover, according to the injection needle unit of the third aspect of the present invention, with regard to the injection needle unit according to the first or second aspect, the opening is provided on the side of the shorter length of the transverse section of the needle base body when looking down from above. Therefore, the size of the opening can be reduced, and simultaneously, the size of the lid can be reduced.

Moreover, according to the injection needle unit of the fourth aspect of the present invention, with regard to the injection needle unit according to any one the first to third aspects, the needle base body has a recess formed therein, and the opening is provided at the bottom portion of the recess, and the recess is formed relatively larger than the opening. Therefore, the enclosing of the opening by the lid can be accomplished easily.

Moreover, according to the injection needle unit of the fifth aspect of the present invention, with regard to the injection needle unit according to the fourth aspect, the lid is formed in a taper shape so that the size becomes thinner, from a base end portion to be engaged with the recess, toward a tip portion for enclosing the opening. Therefore, the above effect can be improved.

Moreover, according to the injection needle unit of the sisth aspect of the present invention, with regard to the injection needle unit according to any one of the first to fifth aspects, the lid is a solidified sealing agent. Therefore, the separate preparation of the lid is not required, whereby the number of components can be reduced, and the assembling work can be facilitated.

Moreover, according to the injection needle unit of the seventh aspect of the present invention, with regard to the injection needle unit according to the sixth aspect, the sealing agent is an adhesive. Therefore, the above effect can be accomplished more securely.

Moreover, according to the injection needle unit of the eighth aspect of the present invention, with regard to the injection needle unit according to any one the first to fifth aspects, the needle base body and the lid have been formed integrally in advance. Therefore, the number of components can be reduced, and the assembling work can be facilitated.

Moreover, according to the injection needle unit of the ninth aspect of the present invention, with regard to the injection needle unit according to any one of the first to eighth aspects, the plurality of needle pieces is configured so as to form multiple rows in the longitudinal direction/a single row in the lateral direction. Therefore, it is possible to manufacture the injection needle unit easily, in which the plurality of needle pieces is configured in a row in the lateral direction.

Moreover, according to the injection needle unit of the tenth aspect of the present invention, with regard to the injection needle unit according to any one of the first to eighth aspects, the plurality of needle pieces is configured so as to form multiple rows in the longitudinal direction/ multiple rows in the lateral direction. Therefore, it is possible to manufacture the injection needle unit easily, in which the plurality of needle pieces is configured in the longitudinal and the lateral directions.

Moreover, according to the injection needle unit of the eleventh aspect of the present invention, with regard to the injection needle unit according to any one of the first to tenth aspects, a tip of each of the plurality of needle pieces has been formed as a slant edge surface, and the oriented direction of each of the slant edge surface is irregularly arranged. Therefore, it is possible to perform the injection of the medicinal solution from various directions.

Moreover, according to the injection needle unit of the twelfth aspect of the present invention, with regard to the injection needle unit according to any one of the first to tenth aspects, a tip of each of the plurality of needle pieces has been formed as a slant edge surface, and the oriented direction of the slant edge surface of each of the plurality of needle pieces is regularly arranged. Therefore, it is possible to perform the injection of the medicinal solution in a predetermined direction.

Moreover, according to the injection needle unit of the thirteenth aspect of the present invention, with regard to the injection needle unit according to the twelfth aspect, the slant edge surfaces of all of the plurality of needle pieces are oriented in the same direction. Therefore, it is possible to perform the injection of the medicinal solution in a predetermined direction.

Moreover, according to the injection needle unit of the fourteenth aspect of the present invention, with regard to the injection needle unit of the twelfth aspect, the plurality of needle pieces is configured so as to form multiple rows in the longitudinal direction/multiple rows in the lateral direction, and the slant edge surfaces of the needle pieces other than the center needle piece are oriented inwardly in the radial direction or outwardly in the radial direction. Therefore, it is possible to perform the injection of the medicinal solution in a predetermined direction.

And moreover, according to an injection device of the fifteenth aspect of the present invention, there is provided with: a syringe; and the injection needle unit according to any one of the first to fourteenth aspects, attached to a tip of the syringe. Therefore, it is possible to easily provide an injection device with the injection needle unit provided with a plurality of needle pieces.

MODE(S) FOR CARRYING OUT THE INVENTION

Now, a first embodiment of the present invention will be explained with reference to FIG. 1 to FIG. 5.

Figure 1:
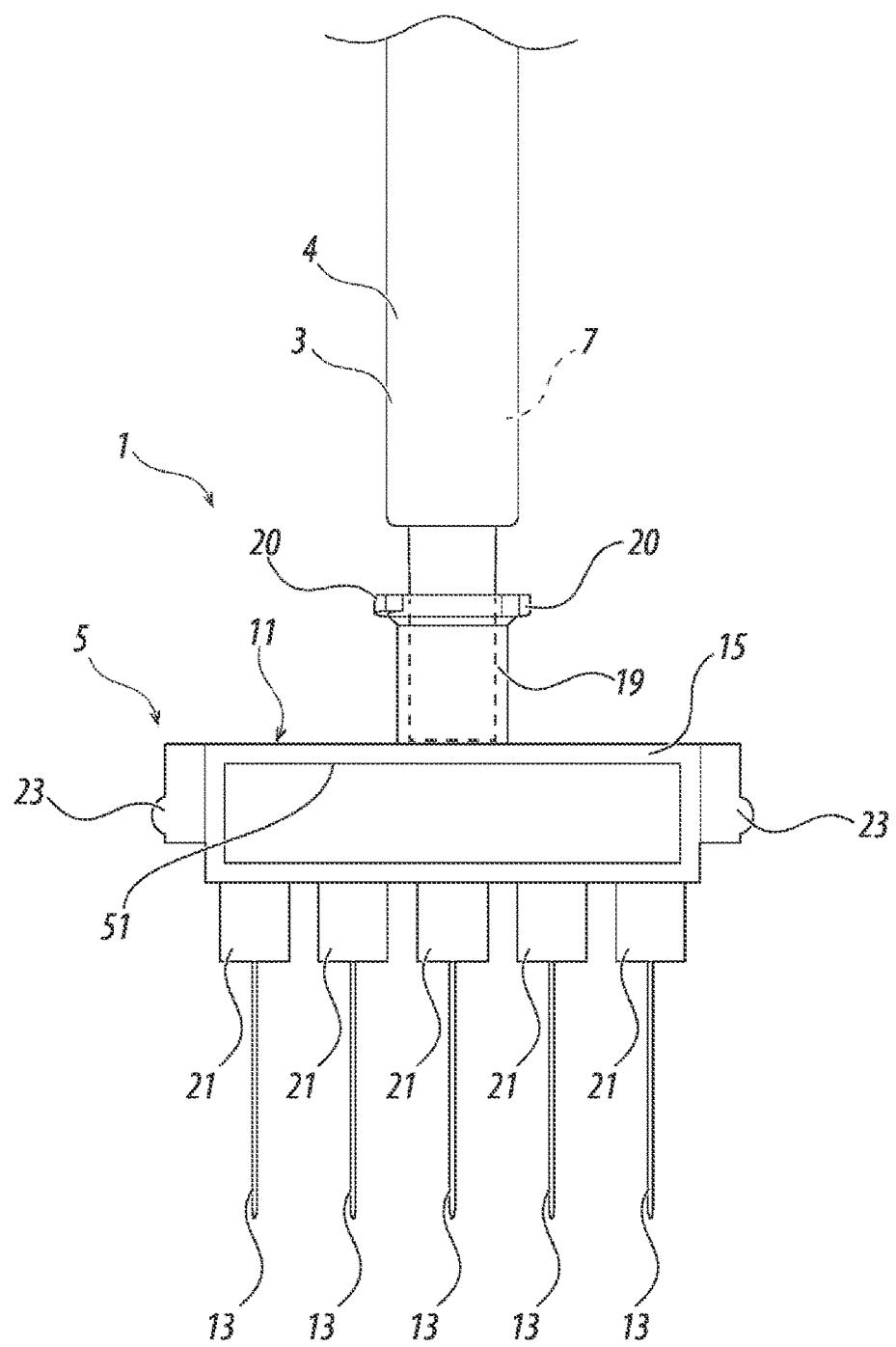
FIG. 1 is a front view showing a using state of an injection needle unit and an injection device according to a first embodiment of the present invention.

As illustrated in FIG. 1, an injection device 1 according to the first embodiment is composed of a syringe 3, and an injection needle unit 5 connected to a tip of the syringe 3. The syringe 3 is composed of a cylinder 4, and a piston (not shown) accommodated to be movable in the cylinder 4. A medicinal solution 7 has been sucked into and retained in the cylinder 4, and with the press operation of the piston, the medicinal solution 7, which has been sucked into and retained in the cylinder 4, is supplied to the side of the injection needle unit 5, whereby the injection is performed.

Figure 2:
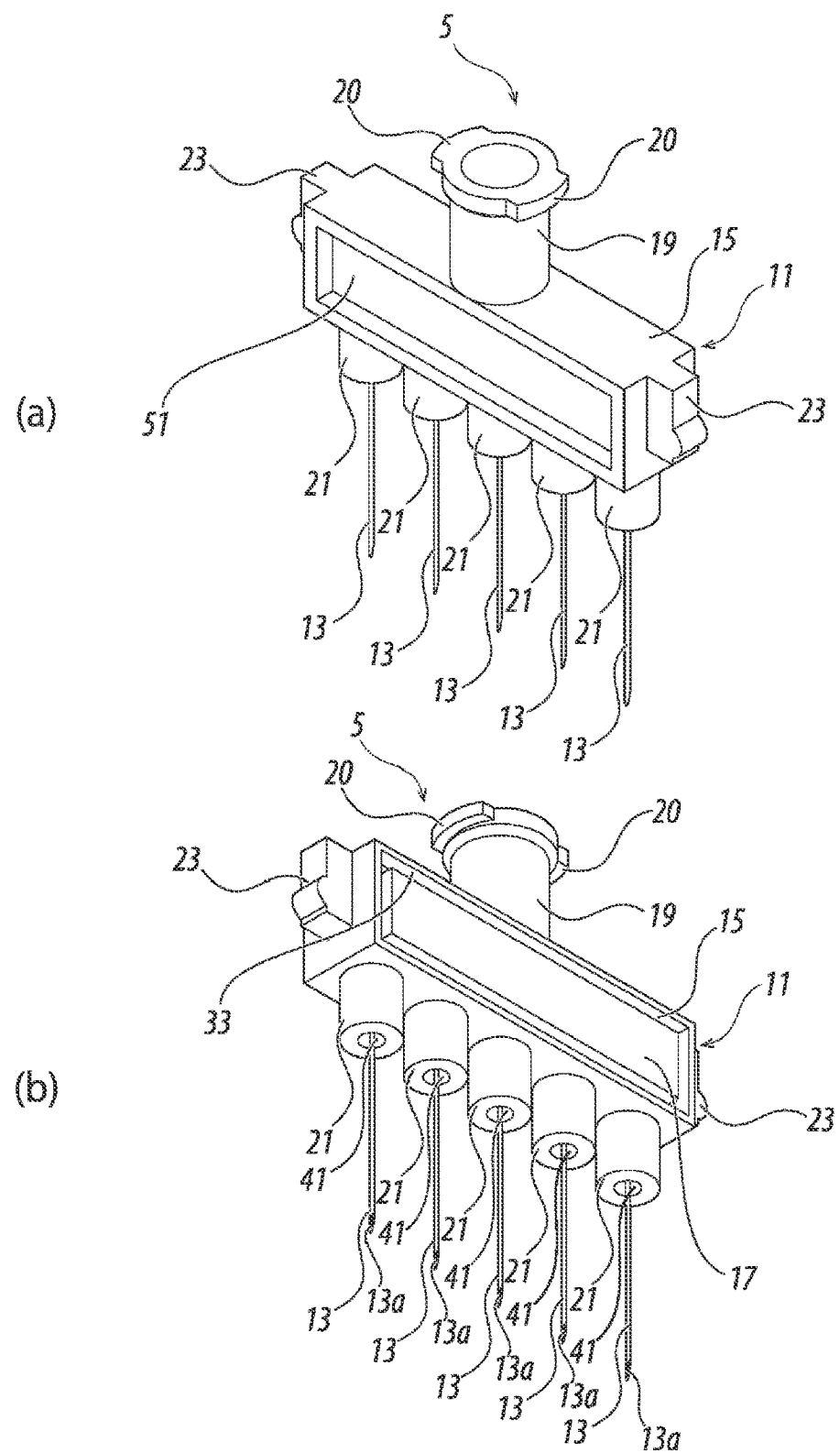
FIG. 2(a) is a perspective view of the injection needle unit as seen from the front upper side.
FIG. 2(b) is a perspective view of the injection needle unit as seen from the rear lower side, according to the first embodiment of the present invention.
Figure 3:
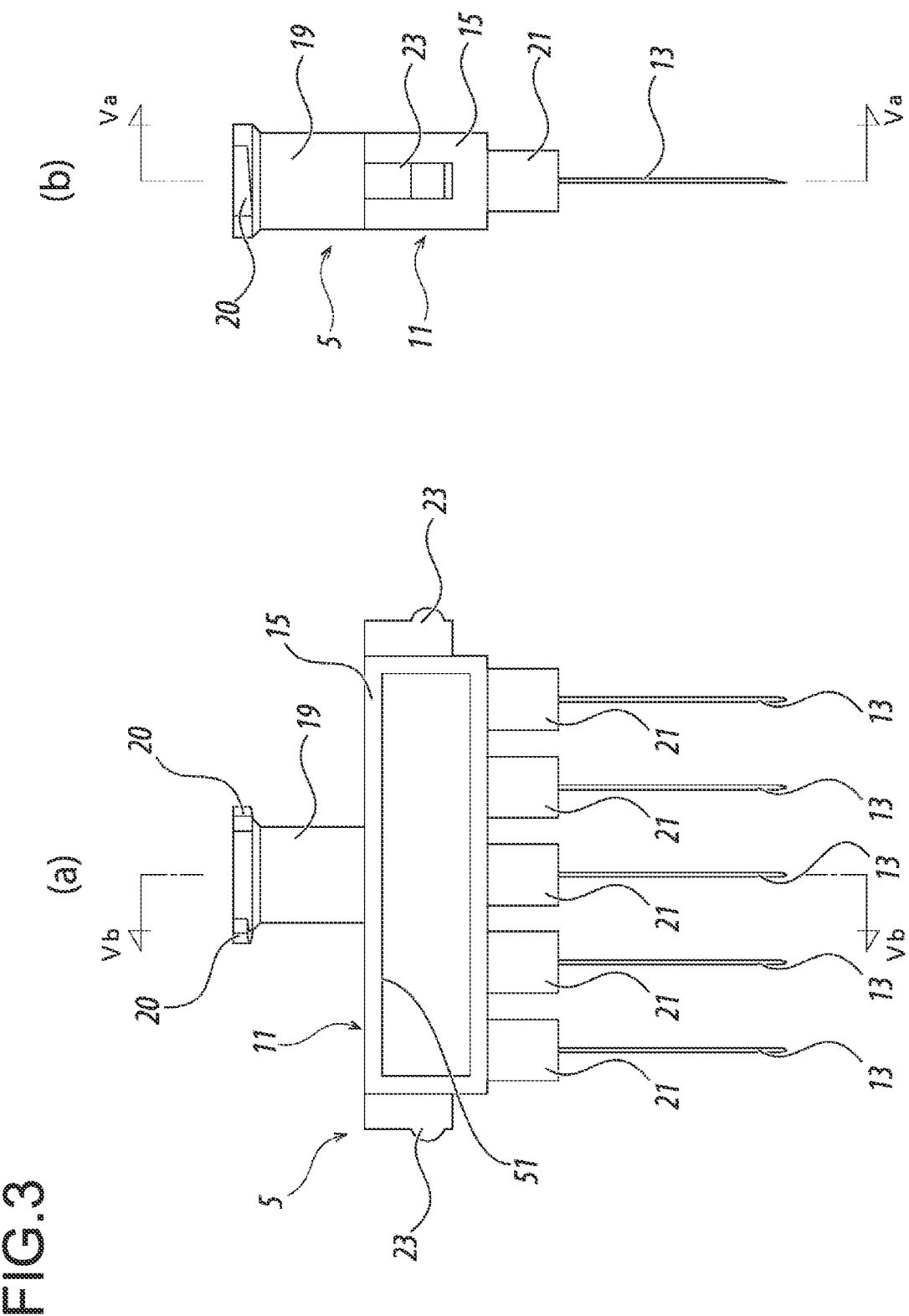
FIG. 3(a) is a front view of the injection needle unit.
FIG. 3(b) is a right side view of the injection needle unit, according to the first embodiment of the present invention.
Figure 4:
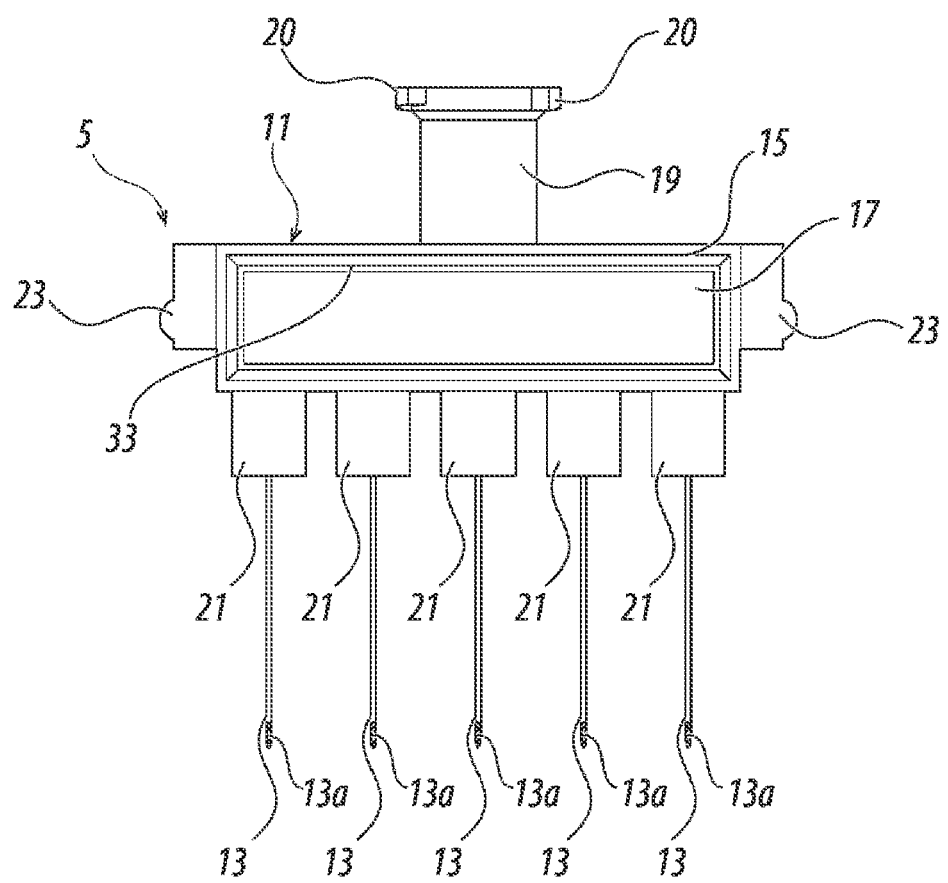
FIG. 4 is a rear view of the injection needle unit according to the first embodiment of the present invention.
Figure 5:
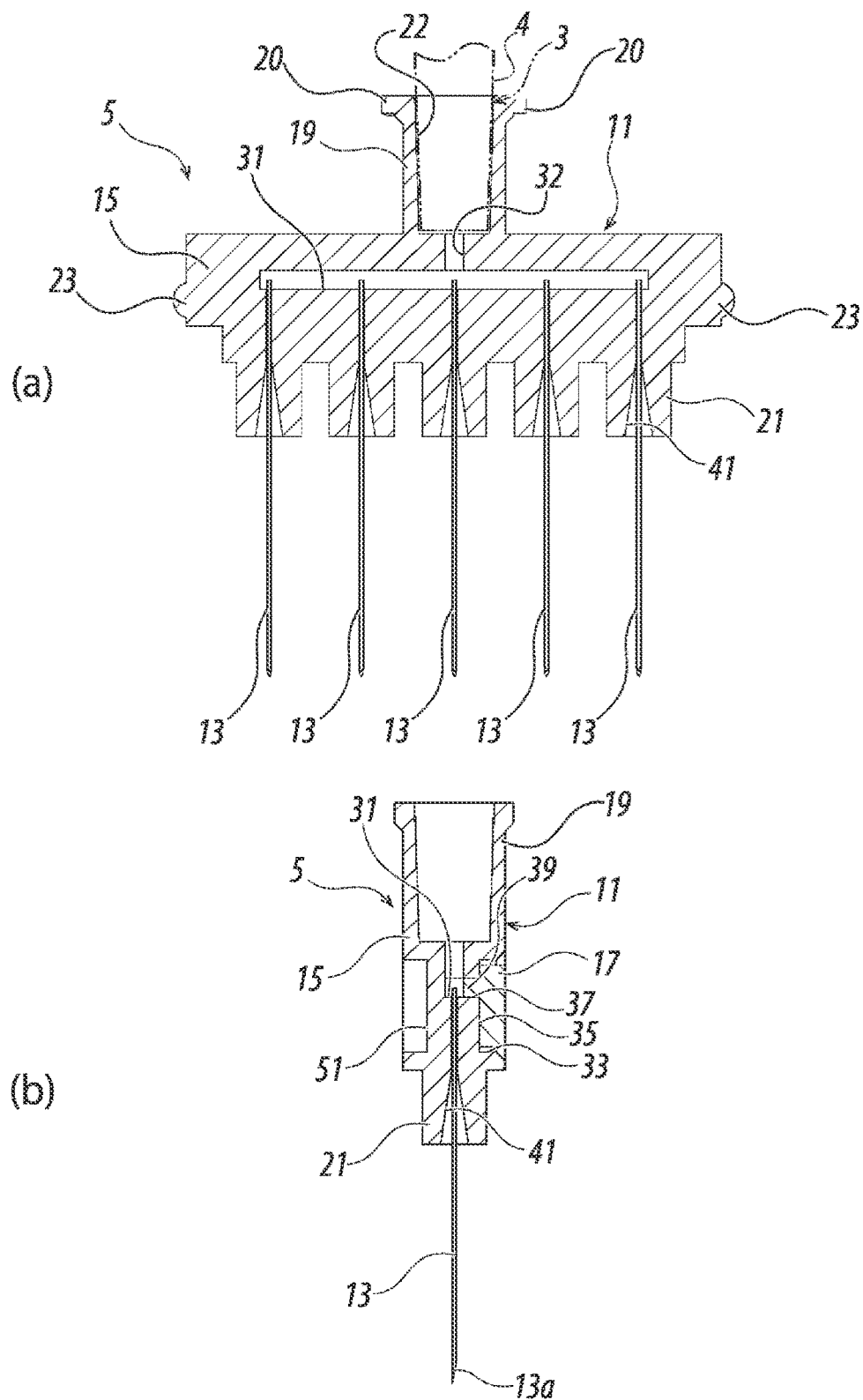
FIG. 5(a) is a sectional view as seen by Va-Va of FIG. 3(b)
FIG. 5(b) is a sectional view as seen by Vb-Vb of FIG. 3(a), according to the first embodiment of the present invention.

As illustrated in FIG. 1 to FIG. 5, the injection needle unit 5 is composed of a needle base 11, and a plurality of (in the present embodiment, with the configuration of five rows in the longitudinal direction/a single row in the lateral direction, in total five) needle pieces 13, respectively attached to the needle base 11. As illustrated in FIG. 2, FIG. 4 and FIG. 5, the needle base 11 is composed of a needle base body 15, and a lid 17 for enclosing an opening, which will be explained in details afterwards, formed in the needle base body 15.

As illustrated in FIG. 3, the needle base body 15 is provided, at the upper portion as seen in FIG. 3, with a syringe connecting portion 19 substantially in a hollow cylindrical shape, and a hollow portion 22 is formed in the syringe connecting portion 19. As illustrated in FIG. 1 and FIG. 5, the tip portion of the cylinder 4 of the syringe 3 is inserted into the hollow portion 22. As illustrated in FIG. 5, the hollow portion 22 is in a taper shape, so that the diameter becomes gradually and slightly smaller from the upper part toward the lower part as seen in FIG. 5. On the other hand, the tip portion of the cylinder 4 is also in a taper shape, so that the diameter becomes gradually and slightly smaller toward the tip. Thus, the cylinder 4 is inserted tightly into the hollow portion 22.

There are lure-lock connecting projections 20, 20, protrusively provided, respectively, opposing to each other at the angle of 180 degrees, on the both sides of the outer peripheral portion of the tip of the syringe connecting portion 19. Where, instead of the syringe 3 as described above, any other type of syringe (not shown) provided with a lure-lock mechanism is used, then, the injection needle unit 5 and the syringe (not shown) are connected to each other by using the lure-lock connecting projections 20, 20.

For example, as illustrated in FIG. 3(a), FIG. 4 and FIG. 5(a), a plurality of (in the first embodiment, five) needle piece connecting portions 21 is disposed at constant intervals, with the configuration of five rows in the longitudinal direction/a single row in the lateral direction (the right/left direction of FIG. 3(a)), at the lower portion of the needle base body 15 as seen in FIG. 3(a). Each of the needle pieces 13, which has been explained as above, is mounted in each of the needle piece connecting portions 21, respectively.

As illustrated in FIG. 3(a), projections 23, 23 are protrusively provided, at the both ends in the widthwise direction (the right/left direction of FIG. 3(a)) of the needle base body 15. The projections 23, 23 serve as locking members when a cap (not shown) is crowned.

As illustrated in FIG. 5, a medicinal solution accommodation space 31 is provided in the inside of the needle base body 15, and a communication hole 32 is provided for communicating between the medicinal solution accommodation space 31 and the hollow portion 22. The medicinal solution 7, which has been supplied from the syringe 3, is then supplied, via the communication hole 32, to the inside of the medicinal solution accommodation space 31, and eventually supplied to all of the needle pieces 13.

As illustrated in FIG. 5(b), a recess 33 is provided on the rear surface side (the right side of FIG. 5(b)) of the needle base body 15. The medicinal solution accommodation space 31 is provided with an opening 37, in the direction (right/left direction of FIG. 5(b)) orthogonal to the axis direction (up/down direction of FIG. 5(b)) of each of the needle pieces 13, that is, at a bottom portion 35 of the recess 33. The size of the opening 37 is set to be smaller than the size of the recess 33.

On the other hand, an enclosing projection 39, for enclosing the opening 37, is formed at a tip side (the left side of FIG. 5(b)) of the lid 17, in a taper shape so that the size becomes thinner toward the tip portion (toward the left side of FIG. 5(b)). With the engagement of the lid 17 with the recess 33, the enclosing projection 39 is inserted into the opening 33. The lid 17 is fixed in the opening 37, by means of adhesion, welding, press fitting, etc.

For reference, the rim of the recess 33 (the right side of FIG. 5(b)) has been chamfered to expand the opening size, whereby the engagement of the lid 17 with the recess 33 is facilitated.

During molding process of the needle base body 15, the opening 33 serves as a mold take-out gate for taking out a slide mold (core), which is used for molding of the medicinal solution accommodation space 31. Moreover, the unused medicinal solution 7 remains in the medicinal solution accommodation space 31, and therefore, preferably, the accommodation volume thereof should be the smallest possible. According to the present embodiment, as illustrated in FIG. 5(a), the height of the medicinal solution accommodation space 31 is set to be slightly higher than the protrusion height of the needle piece 13, and at the same time, as illustrated in FIG. 5(b), the width of the medicinal solution accommodation space 31 is set to be slightly larger than the outer diameter of the needle piece 13. Consequently, the accommodation volume of the medicinal solution accommodation space 31 is set to be the smallest possible, with maintaining the function of supplying of the medicinal solution 7 to all of the needle pieces 13.

For reference, the slide mold (core) for molding the communication hole 32 is taken out from the opening at the upper end of the hollow portion 22.

As illustrated in FIG. 5(b), in the needle base body 15, needle piece attaching through holes 41 are formed, each of which is communicating to the medicinal solution accommodation space 31 and opening on the tip surface (the surface on the lower side of FIG. 5(b)) of the needle piece connecting portion 21. The needle piece 13 is inserted into and fixed in the needle piece attaching through hole 41. The diameter of the tip portion (the lower side of FIG. 5(b)) of the needle piece attaching through hole 41 is gradually enlarged toward the tip side (the lower side of FIG. 5(b)), whereby the needle piece 13 can be inserted easily into the needle piece attaching through hole 41 from the tip end side (the lower side of FIG. 5(b)) during manufacturing of the injection needle unit 5. The needle piece 13 is fixed by adhesive, etc.

As illustrated in FIG. 5(b), a recess 51 is provided on the front surface side (the left side of FIG. 5(b)) of the needle base body 15. The recess 51 is provided for the purpose of downgage for the prevention of sink marks during molding, and for the purpose of weight reduction. Moreover, a slant edge surface 13a is provided at the tip of the needle piece 13, and in the present embodiment, with regard to the five needle pieces 13, each of the slant edge surfaces 13a is all oriented in the same direction.

Next, the function of the first embodiment will be explained.

First, the syringe 3 is in a detached state from the injection needle unit 5, and with the pulling of the piston (not shown), the medicinal solution 7 is sucked into and retained in the cylinder 4, from the tip side of the cylinder 4 of the syringe 3.

Next, the tip portion of the cylinder 4 of the syringe 3 is inserted into the hollow portion 22 of the syringe connecting portion 19. Consequently, the injection needle unit 5 is integrally attached to the tip of the syringe 3.

Next, the all tips of the needle pieces 13 of the injection needle unit 5 are punctured into the skin of a patient (not shown), and the piston (not shown) of the syringe 3 is depressed. Consequently, the medicinal solution 7 in the cylinder 4 is supplied, from the inside of the cylinder 4, via the communication hole 32, to the medicinal solution accommodation space 31, and further supplied, from the medicinal solution accommodation space 31, to all of the needle pieces 13. Thereafter, the intradermal or subcutaneous administration is performed, from all of the needle pieces 13, to the patient (not shown).

Next, the effect of the first embodiment will be explained.

First, with regard to the injection needle unit 5, which is a so-called multiple needle unit provided with a plurality of the needle pieces 13, the structure can be simplified, and the manufacturing thereof can be facilitated.

That is, according to the present embodiment, although the needle base 11 of the injection needle unit 5 is not a single component, this is composed of the needle base body 15 and the lid 17, so the structure is simple. In particular, the needle base body 15 is in a shape provided with substantially all of the structural elements of the needle base 11, and this may be considered as almost a single component. Accordingly, the lid 17 can be provided as a component in a small and very simple shape, and therefore, when seen as a whole, the structure is simplified.

Moreover, both the needle base body 15 and the lid 17 can be molded, for example, by means of injection molding, and therefore, the manufacturing thereof is easy.

During manufacturing, since the opening 37 is provided in the needle base body 15, the slide mold (core) for molding of the medicinal solution accommodation space 31 can be taken out easily. Moreover, as described above, since the lid 17 is in a small and very simple shape, the manufacturing thereof is also easy.

Moreover, in the present embodiment, with regard to the medicinal solution accommodation space 31, which eventually becomes a dead space, the size is set to be the smallest possible, with maintaining the necessary function. Thus, it is possible to reduce the residue volume of the medicinal solution 7, which was not used for the injection.

Moreover, since the size of the medicinal solution accommodation space 31 is set to be the smallest possible, the size of the opening 37 is also small, and the enclosure of such a small-sized opening 37 would be bothersome. However, according to the present embodiment, the recess 33 having relatively a big size is provided, and the opening 37 is disposed at the bottom portion thereof, and on the other hand, the lid 17 is in a taper shape so that the size becomes thinner, from the base end side toward the enclosing projection 39 at the tip. Accordingly, with the engagement of the base end portion of the lid 17 with the recess 33, of which size is relatively large as described above, the enclosing projection 39 can be inserted into the opening 37 easily, whereby the enclosing work of the opening 37 is facilitated.

For reference, the injection needle unit 5 according to the present embodiment is a so-called "multiple needle unit" provided with five injection needle pieces, with the configuration of five rows in the longitudinal direction/a single row in the lateral direction, and therefore, it is possible to perform the injection in a wide area by a single administration, whereby the labor for the injection can be relieved, and the time for the injection can be reduced. Moreover, the unevenness of injection depth of the medicinal solution 7 can be eliminated, and the area where the medicinal solution was not administrated can be reduced.

Next, a second embodiment of the present invention will be explained with reference to FIG. 6 to FIG. 10.

Figure 6:
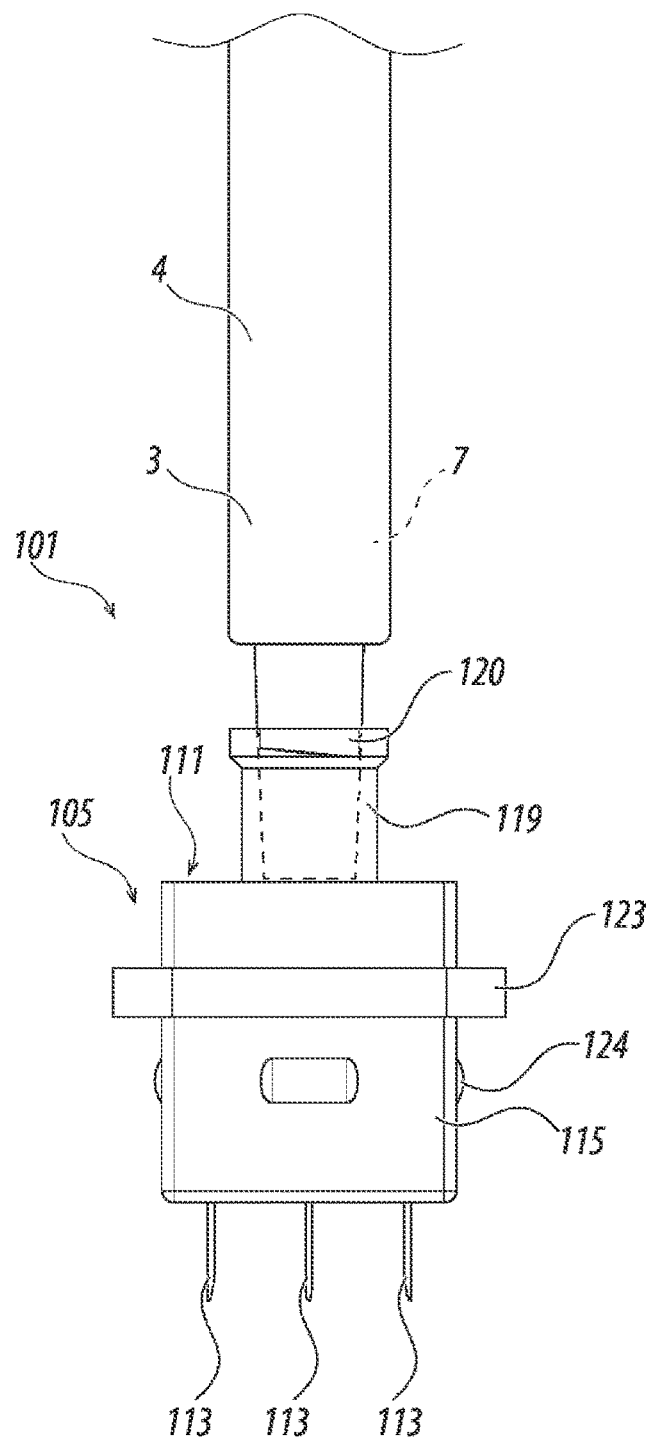
FIG. 6 is a front view showing a using state of an injection needle unit and an injection device according to a second embodiment of the present invention.

Also in the second embodiment, as illustrated in FIG. 6, an injection device 101 is composed of the syringe 3, and an injection needle unit 105 connected to a tip of the cylinder 4 of the syringe 3. The medicinal solution 7 has been sucked into and retained in the cylinder 4, and with the press operation of the piston (not shown), the medicinal solution 7 in the cylinder 4 is supplied to the side of the injection needle unit 105.

As illustrated in FIG. 6 to FIG. 10, the injection needle unit 105 is composed of a needle base 111, and a plurality of (in the present embodiment, with the configuration of three rows in the longitudinal direction/three rows in the lateral direction, in total nine) needle pieces 113, respectively attached to the needle base 111.

Figure 7:
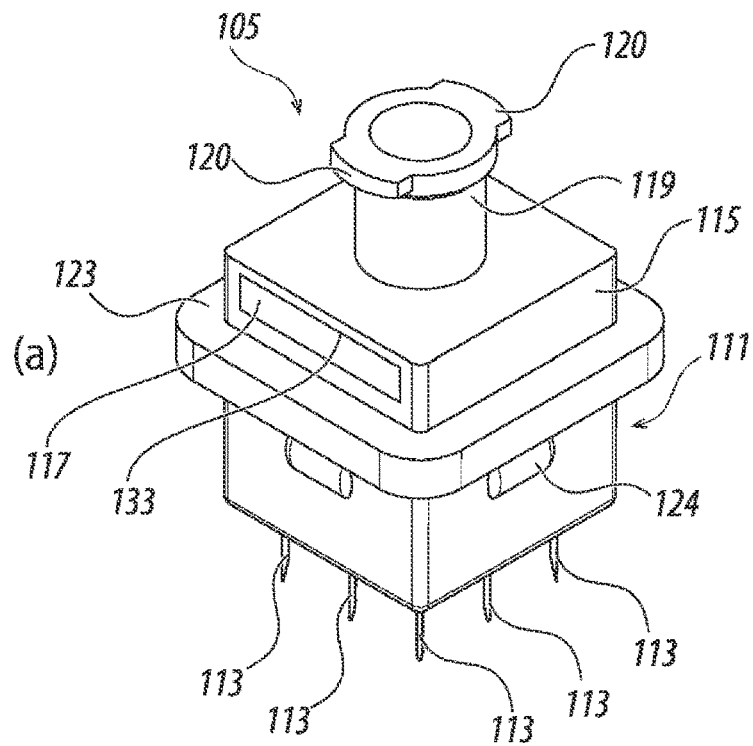
FIG. 7(a) is a perspective view of the injection needle unit as seen from the front upper side.
FIG. 7(b) is a perspective view of the injection needle unit as seen from the rear lower side, according to the second embodiment of the present invention.
Figure 7:
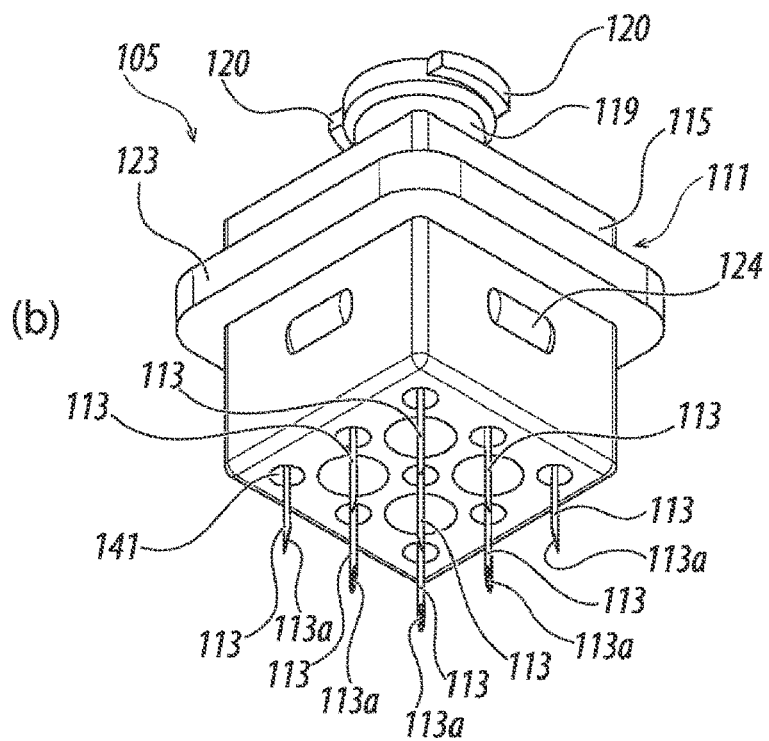
Figure 9:
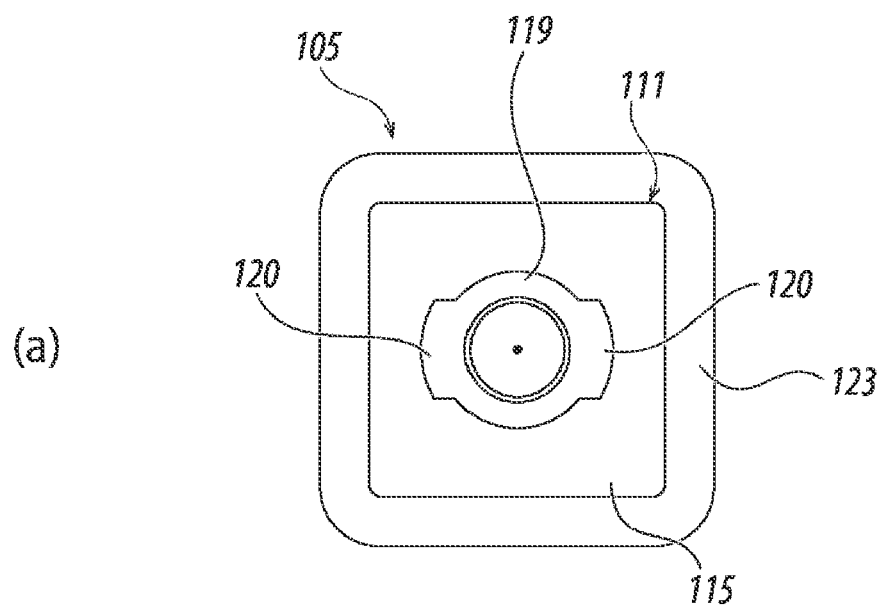
FIG. 9(a) is a plan view of the injection needle unit.
FIG. 9(b) is a bottom view of the injection needle unit, according to the second embodiment of the present invention.
Figure 9:
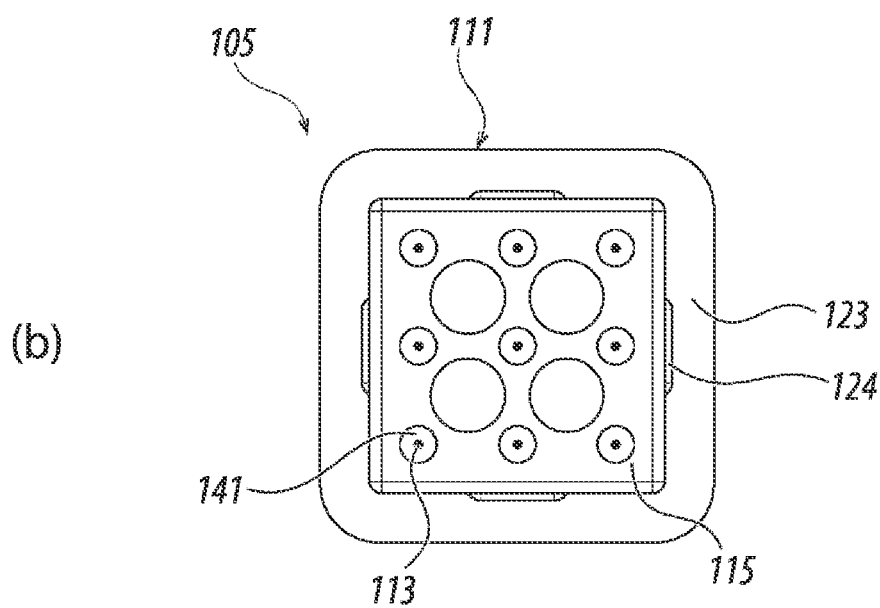
Figure 10:
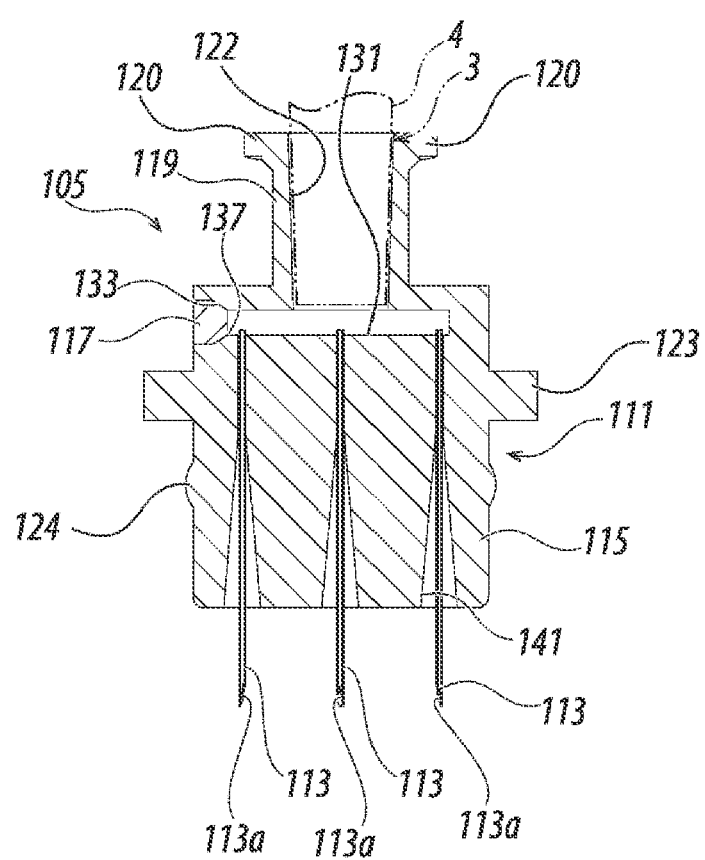
FIG. 10 is a sectional view as seen by X-X of FIG. 8 according to the second embodiment of the present invention.

As illustrated in FIG. 7, FIG. 9 and FIG. 10, the needle base 111 is composed of a needle base body 115, and a lid 117 for enclosing an opening, which will be explained in details afterwards, formed in the needle base body.

Figure 8:
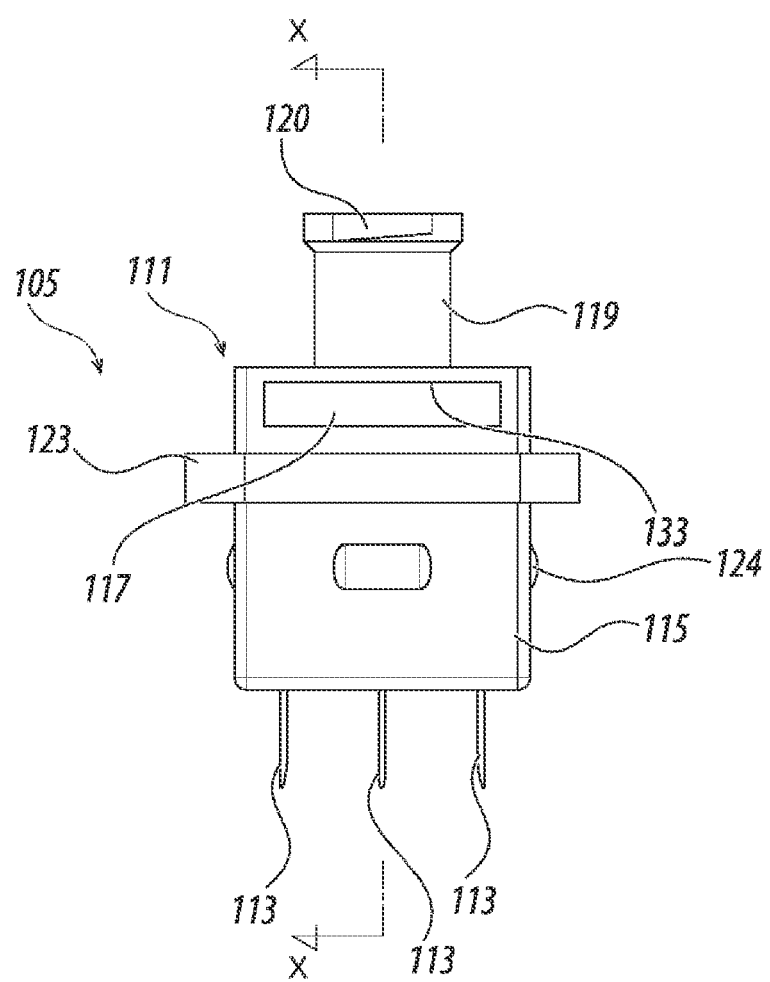
FIG. 8 is a front view of the injection needle unit according to the second embodiment of the present invention.

As illustrated in FIG. 8 and FIG. 10, the needle base body 115 is provided, at the upper portion as seen in the drawings, with a syringe connecting portion 119 substantially in a hollow cylindrical shape. As illustrated in FIG. 10, a hollow portion 122 is formed in the syringe connecting portion 119, and the tip portion of the cylinder 4 of the syringe 3 is inserted into the hollow portion 122. As illustrated in FIG. 10, the hollow portion 122 is in a taper shape, so that the diameter becomes gradually and slightly smaller from the upper part toward the lower part as seen in FIG. 10. On the other hand, the tip portion of the cylinder 4 is also in a taper shape, so that the diameter becomes gradually and slightly smaller toward the tip. Thus, the cylinder 4 is inserted tightly into the hollow portion 122.

There are lure-lock connecting projections 120, 120, protrusively provided, respectively, opposing to each other at the angle of 180 degrees, on the both sides of the outer peripheral portion of the tip of the syringe connecting portion 119. Where, instead of the syringe 3 as described above, any other type of syringe (not shown) provided with a lure-lock mechanism is used, then, the injection needle unit 105 and the syringe (not shown) are connected to each other by using the lure-lock connecting projections 120, 120.

As illustrated in FIG. 6 to FIG. 10, on the outer peripheral side of the needle base body 115, a projection 123 in a shape of a collar is provided, and also four projections 124, 124, 124, 124 are provided. These four projections 124, 124, 124, 124 serve as engagement projections to be engaged, when a cap (not shown) is crowned, with corresponding engagement recesses provided on the cap, and further, the projection 123 serves as a stopper on which the end of the cap abuts.

As illustrated in FIG. 10, a medicinal solution accommodation space 131 is provided in the inside of the needle base body 115. Similar to the case of the first embodiment as described above, the accommodation volume of the medicinal solution accommodation space 131 is set to be the smallest possible, with maintaining the necessary function. A recess 133 is provided on the front surface side (the left side of FIG. 10) of the needle base body 115. The medicinal solution accommodation space 131 is provided with an opening 137, in the direction (right/left direction of FIG. 10 orthogonal to the axis direction (up/down direction of FIG. 10) of each of the needle pieces 113, that is, on the bottom side of the recess 133. The size of the opening 137 is set to be smaller than the size of the recess 133.

On the other hand, the lid 117 is in a taper shape so that the size becomes thinner toward the tip portion (toward the right side of FIG. 10). With the engagement of the lid 117 with the recess 133, the opening 137 is enclosed by the tip portion of the lid 117. Since it is sufficient to engage the lid 117 with the recess 133, of which size is relatively larger than the size of the opening 137, the engagement work is easy.

As illustrated in FIG. 8, FIG. 9 and FIG. 10, a plurality of needle piece attaching through holes 141 is provided (in the present embodiment, three rows in the longitudinal direction/three rows in the lateral direction, in total nine), on the lower side (the near side in the perpendicular direction against the drawing sheet of FIG. 9(*b*)) of the medicinal solution accommodation space 131 of the needle base body 115. Each of the needle pieces 113 as described above is attached to each of the needle piece attaching through holes 141, respectively. The diameter of the tip portion (the lower side of FIG. 10) of the needle piece attaching through hole 141 is gradually enlarged toward the tip side (the lower side of FIG. 10), whereby the needle piece 113 can be inserted easily into the needle piece attaching through hole 141 from the tip end side (the lower side of FIG. 10) during manufacturing of the injection needle unit 105.

For reference, the other structure is substantially the same as that of the first embodiment described above, and the same reference signs will be allotted to the same elements in the drawings, and the explain thereof will be omitted.

Moreover, a slant edge surface 113*a* is provided at the tip of each of the plurality of needle pieces 113, and with regard to the eight needle pieces 113 disposed at the outer positions in FIG. 9(*b*), each of the slant edge surfaces 113*a* is all oriented inwardly in the radial direction. The slant edge surface 113*a* of the needle piece 113 at the center position is oriented in a predetermined direction.

According to the second embodiment, it is also possible to achieve substantially the same function and effect as those of the first embodiment described above.

Moreover, since there are nine needle pieces 113 configured to form three rows in the longitudinal direction/three rows in the lateral direction, it is possible to perform injection effectively, in the area wider than that of the first embodiment.

Figure 11:
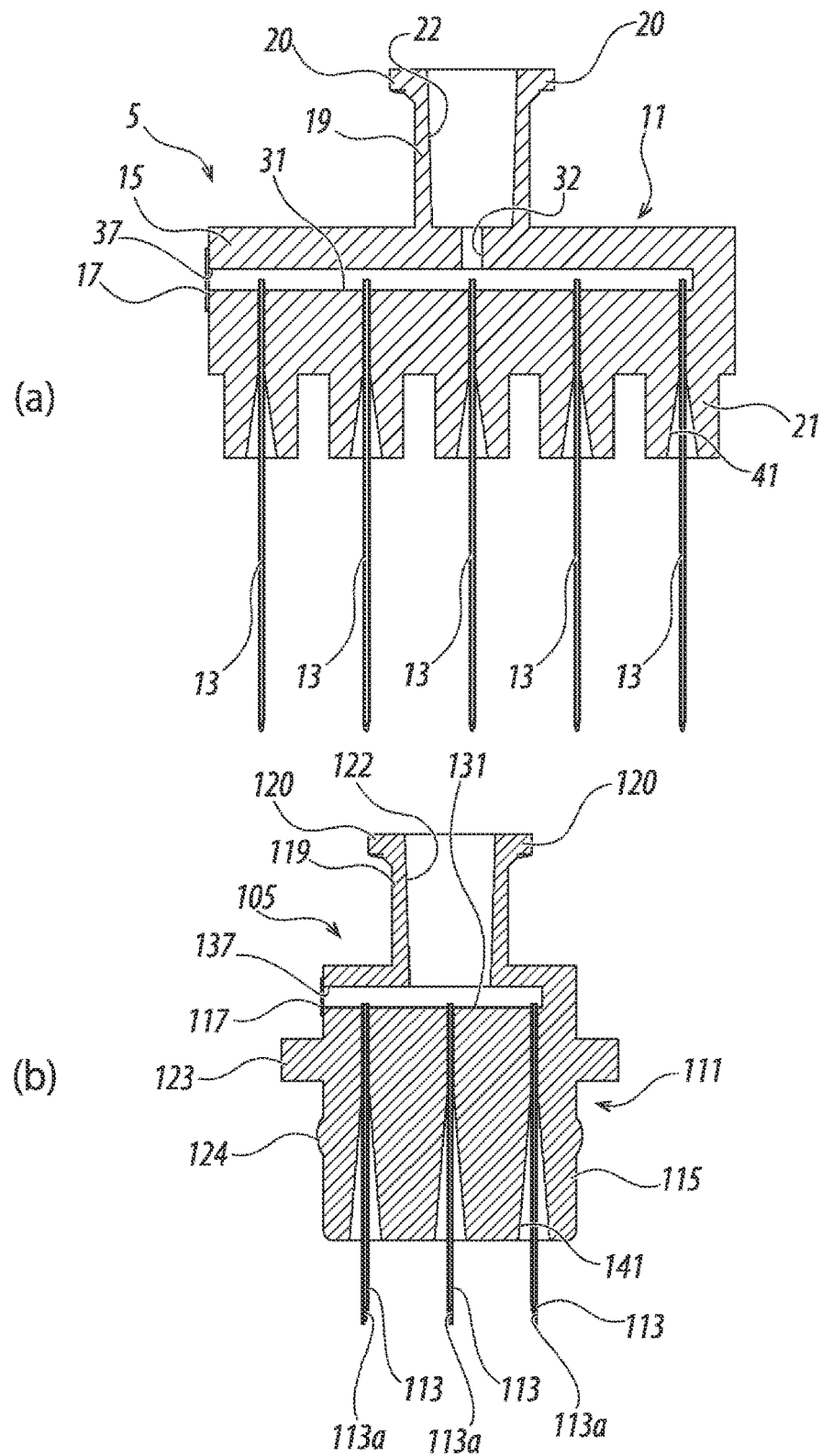
FIG. 11(a) is a vertical sectional view of an injection needle unit according to a third embodiment of the present invention.
FIG. 11(b) is a vertical sectional view of an injection needle unit according to a fourth embodiment of the present invention.

Next, a third embodiment of the present invention will be explained with reference to FIG. 11(*a*). In the first embodiment as described above, the opening 37 of the medicinal solution accommodation space 31 is provided on the wider side (on the side of the longer length of the cross-sectional rectangular surface) of the medicinal solution accommodation space 31. However, in the present embodiment, the opening 37 is provided on the narrower side (on the side of the shorter length of the cross-sectional rectangular surface, the left end of FIG. 11(*a*)) of the medicinal solution accommodation space 31. Moreover, in the first embodiment, the recess 33 is provided, of which bottom is provided with the opening 37. However, in the present embodiment, there is no such a recess provided. Moreover, in the first embodiment, a molded product made of synthetic resin is used as the lid 17. However, in the present embodiment, the lid 17 is, for example, an adhesive tape made of synthetic resin or aluminum.

For reference, the other structure is substantially the same as that of the first embodiment described above, and the same reference signs will be allotted to the same elements in the drawings, and the explain thereof will be omitted.

Accordingly, it is possible to achieve substantially the same effect as that of the first embodiment described above. Further, the size of the opening 37 can be reduced, and consequently, the size of the lid 17 can also be reduced. Moreover, the lid 17 is not a molded product made of synthetic resin, but an adhesive tape made of synthetic resin or aluminum, and therefore, the manufacturing thereof is easy, and the assembling work can be simplified. Moreover, when considering as a molded product, only a single component is sufficient.

Next, a fourth embodiment of the present invention will be explained with reference to FIG. 11(*b*). In the second embodiment as described above, the opening 137 is provided at the bottom portion of the recess 133. However, in the present embodiment, there is no such a recess provided. Moreover, in the second embodiment, a molded product made of synthetic resin is used as the lid 117 for enclosing the opening 137. However, in the present embodiment, the lid 117 is, for example, an adhesive tape made of synthetic resin or aluminum.

For reference, the other structure is substantially the same as that of the second embodiment described above, and the same reference signs will be allotted to the same elements in the drawings, and the explain thereof will be omitted.

Accordingly, it is possible to achieve substantially the same effect as that of the second embodiment described above. Further, the lid 117 is not a molded product made of synthetic resin, but an adhesive tape made of synthetic resin or aluminum, and therefore, the manufacturing thereof is easy, and the assembling work can be simplified. Moreover, when considering as a molded product, only a single component is sufficient.

Figure 12:
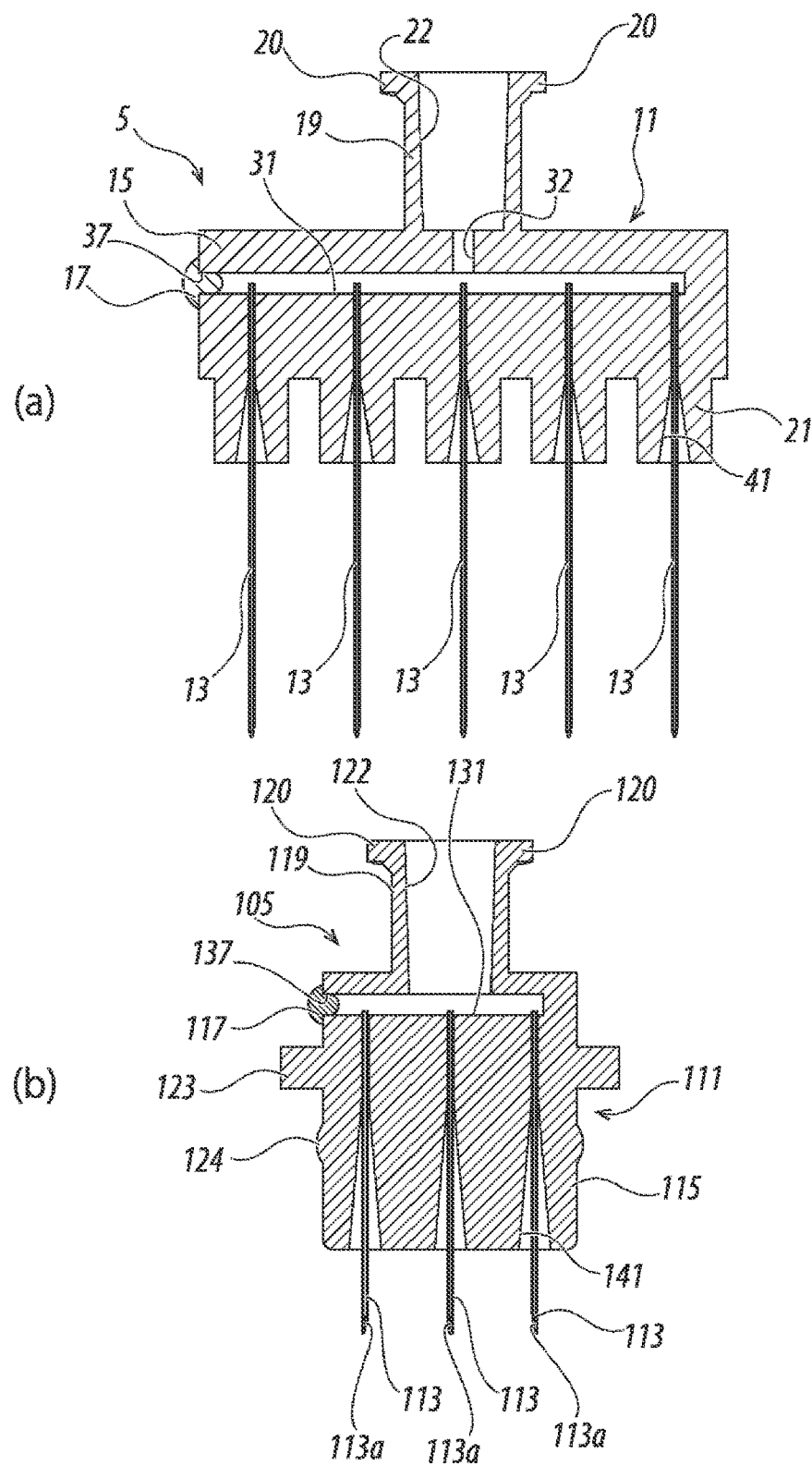
FIG. 12(a) is a vertical sectional view of an injection needle unit according to a fifth embodiment of the present invention.
FIG. 12(b) is a vertical sectional view of an injection needle unit according to a sixth embodiment of the present invention.

Next, a fifth embodiment of the present invention will be explained with reference to FIG. 12(a). In the third embodiment as described above, the adhesive tape made of synthetic resin or aluminum is used as the lid 17. However, in the present embodiment, an adhesive is used for that purpose.

For reference, the other structure is substantially the same as that of the third embodiment described above, and the same reference signs will be allotted to the same elements in the drawings, and the explain thereof will be omitted.

Accordingly, it is possible to achieve substantially the same effect as that of the third embodiment described above.

Next, a sixth embodiment of the present invention will be explained with reference to FIG. 12(b). In the fourth embodiment as described above, the adhesive tape made of synthetic resin or aluminum is used as the lid 117. However, in the present embodiment, an adhesive is used for that purpose.

For reference, the other structure is substantially the same as that of the fourth embodiment described above, and the same reference signs will be allotted to the same elements in the drawings, and the explain thereof will be omitted.

Accordingly, it is possible to achieve substantially the same effect as that of the fourth embodiment described above.

Figure 13:
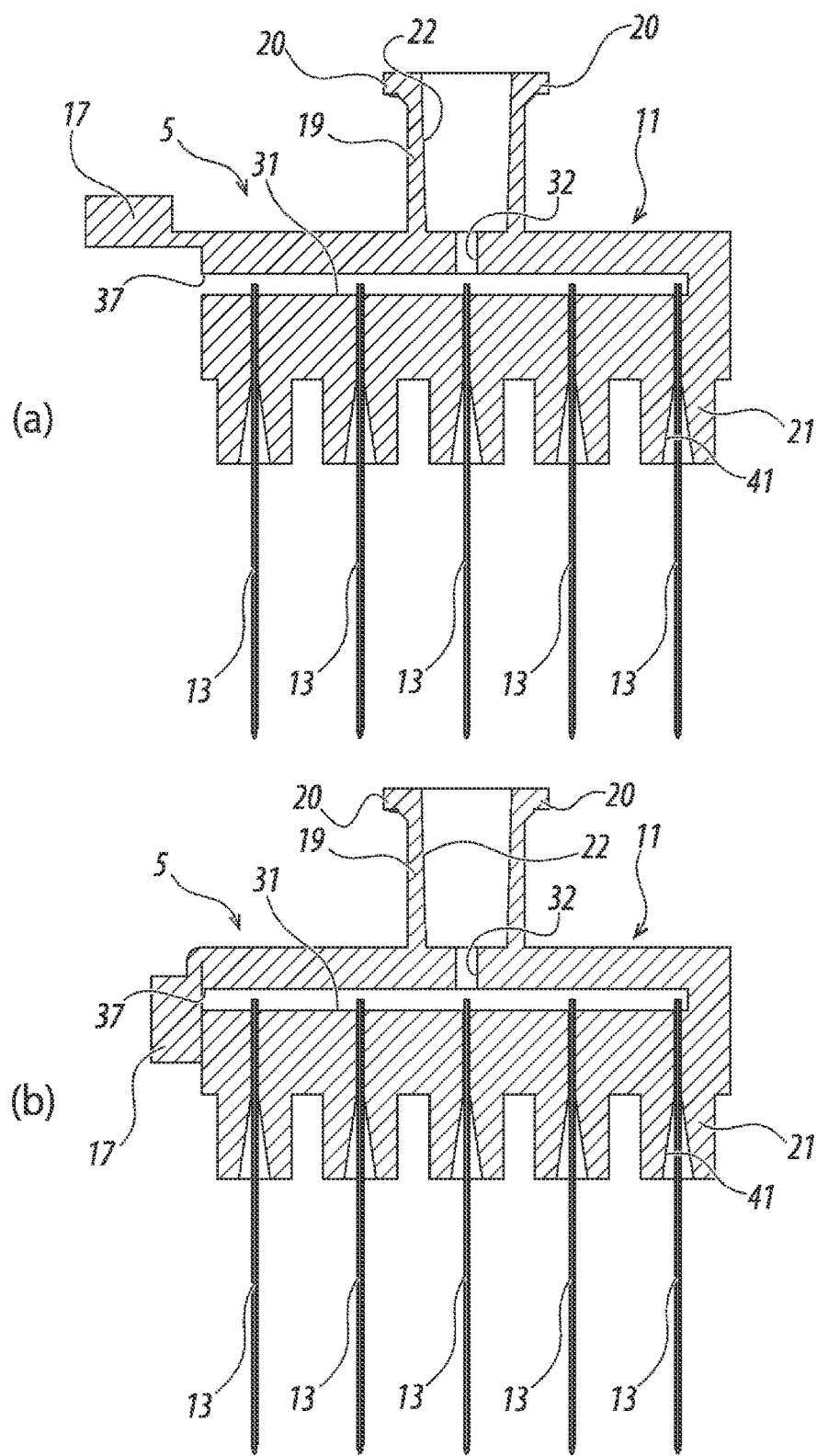
FIG. 13(a) is a vertical sectional view of an injection needle unit before an opening is enclosed by a lid.
FIG. 13(b) is a vertical sectional view of the injection needle unit in a state that the opening is enclosed by the lid, according to a seventh embodiment of the present invention.

Next, a seventh embodiment of the present invention will be explained with reference to FIG. 13. In the present embodiment, as illustrated in FIG. 13(a), the lid 17 has been provided integrally with the needle base body 15. Thus, as illustrated in FIG. 13(b), after the slide mold is taken out of the medicinal solution accommodation space 33, the lid 17 is bent, and also welded or adhered, whereby the opening 37 is enclosed.

For reference, the other structure is substantially the same as that of the third embodiment described above, and the same reference signs will be allotted to the same elements in the drawings, and the explain thereof will be omitted.

Accordingly, it is possible to achieve substantially the same effect as that of the third embodiment described above. Further, since it is not necessary to provide the lid 17 separately as a molded product, a tape or an adhesive, etc., the manufacturing thereof is easy, and the assembling work can be simplified.

Figure 14:
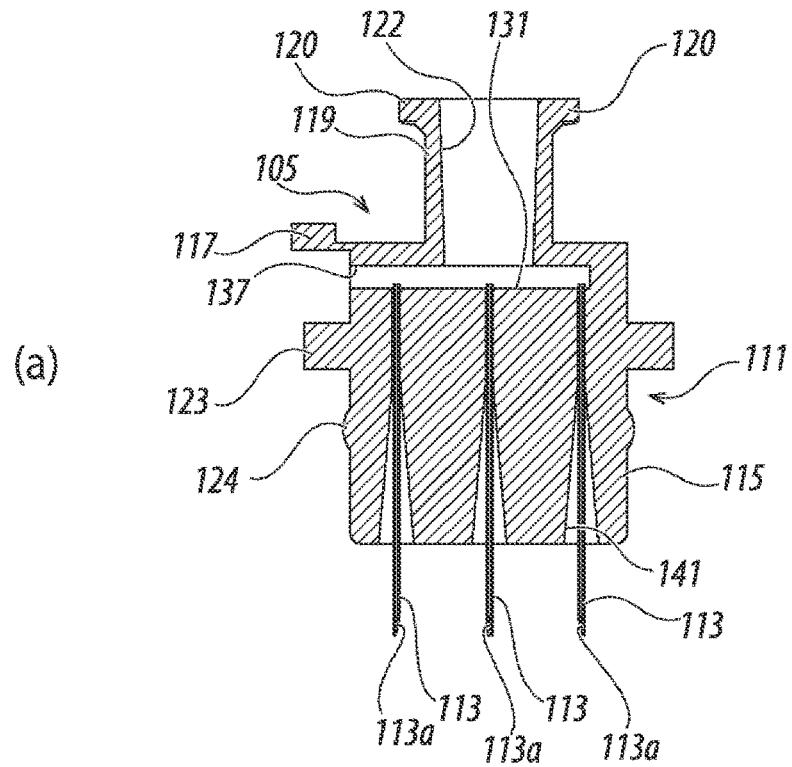
FIG. 14(a) is a vertical sectional view of an injection needle unit before an opening is enclosed by a lid.
FIG. 14(b) is a vertical sectional view of the injection needle unit in a state that the opening is enclosed by the lid, according to an eighth embodiment of the present invention.
Figure 14:
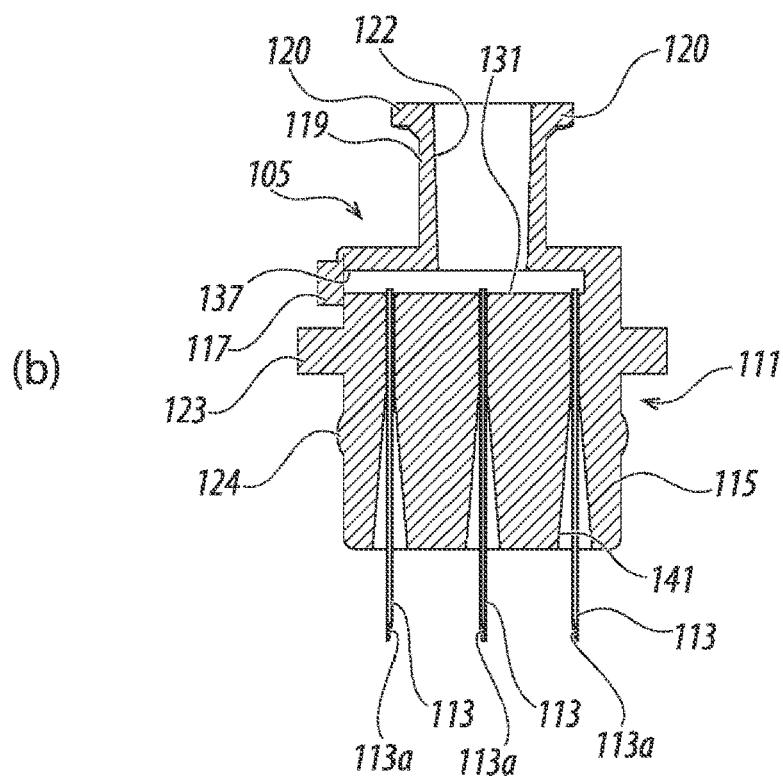

Next, an eighth embodiment of the present invention will be explained with reference to FIG. 14. In the present embodiment, as illustrated in FIG. 14(a), the lid 117 has been provided integrally with the needle base body 115. Thus, as illustrated in FIG. 14(b), after the slide mold is taken out of the medicinal solution accommodation space 133, the lid 117 is bent, and also welded or adhered, whereby the opening 137 is enclosed.

For reference, the other structure is substantially the same as that of the fourth embodiment described above, and the same reference signs will be allotted to the same elements in the drawings, and the explain thereof will be omitted.

Accordingly, it is possible to achieve substantially the same effect as that of the fourth embodiment described above. Further, since it is not necessary to provide the lid 117 separately as a molded product, a tape or an adhesive, etc., the manufacturing thereof is easy, and the assembling work can be simplified.

Figure 15:
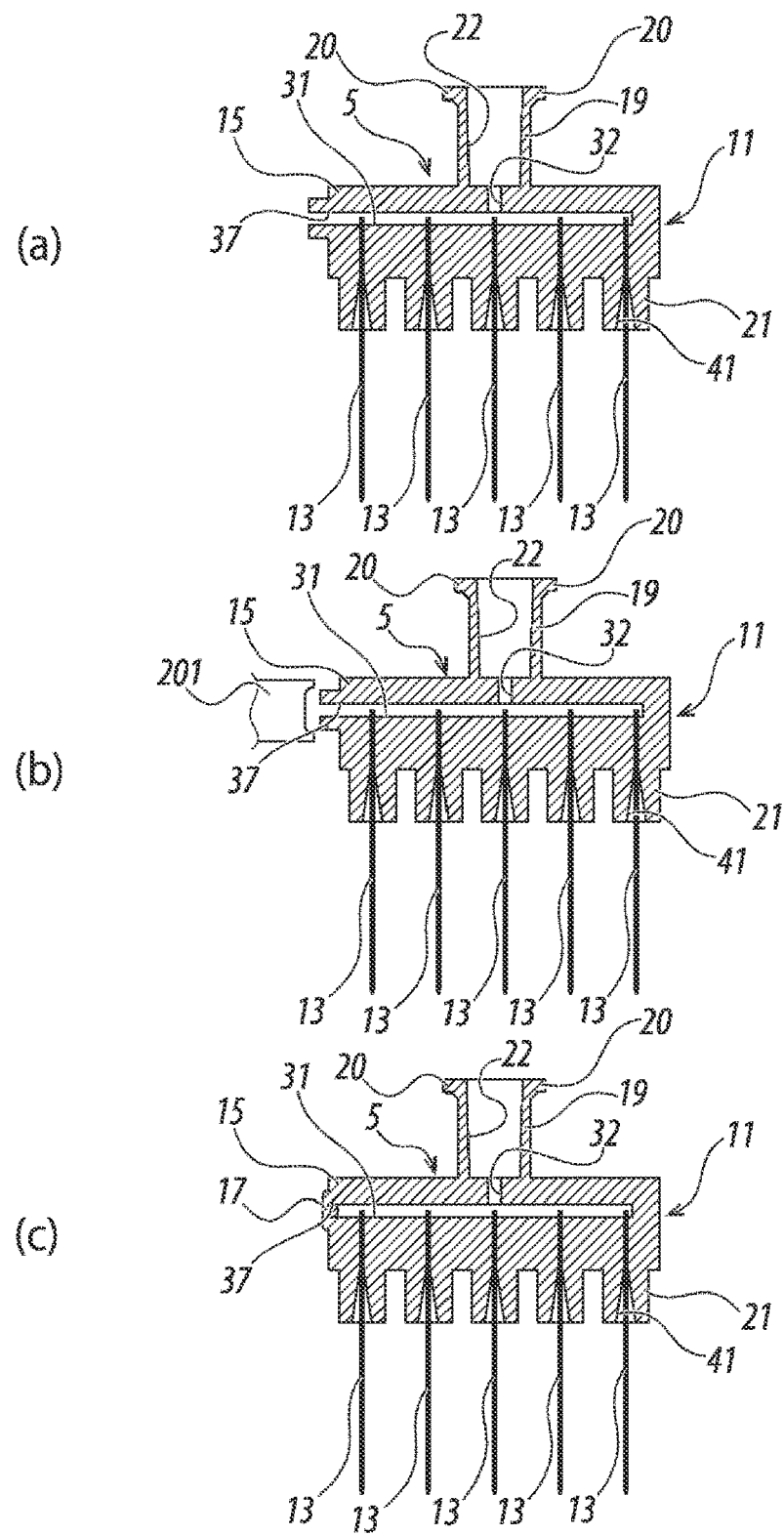
FIG. 15(a) is a vertical sectional view of an injection needle unit before an opening is enclosed.
FIG. 15(b) is a vertical sectional view of the injection needle unit in a state that a position of a lid is being welded.
FIG. 15(c) is a vertical sectional view of the injection needle unit in a state that the opening is enclosed by the lid, according to a ninth embodiment of the present invention.

Next, a ninth embodiment of the present invention will be explained with reference to FIG. 15. In the present embodiment, first, as illustrated in FIG. 15(a), the portion, in which the opening 37 of the needle base body 15 has been formed, is protruding. Next, as illustrated in FIG. 15(b), the protruding portion as described above is welded, for example by using an ultrasonic welding apparatus 201. Consequently, as illustrated in FIG. 15(c), the welded portion becomes the lid 17, whereby the opening 37 is enclosed.

For reference, the other structure is substantially the same as that of the third embodiment described above, and the same reference signs will be allotted to the same elements in the drawings, and the explain thereof will be omitted.

Accordingly, it is possible to achieve substantially the same effect as that of the third embodiment described above. Moreover, since it is not necessary to provide the lid 17 as a separate molded product, the manufacturing thereof is easy, and the assembling work can be simplified.

Figure 16:
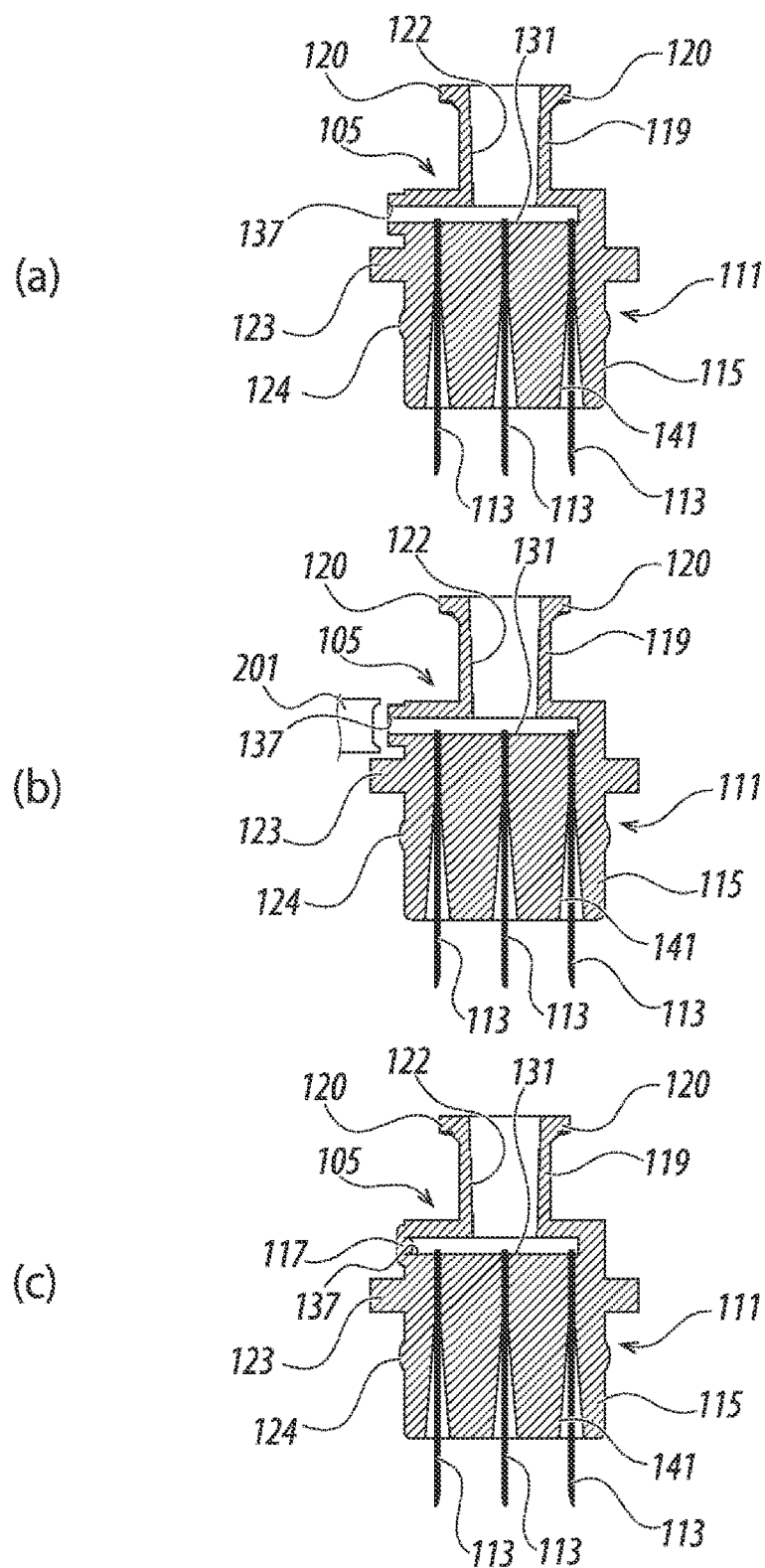
FIG. 16(a) is a vertical sectional view of an injection needle unit before an opening is enclosed.
FIG. 16(b) is a vertical sectional view of the injection needle unit in a state that a position of a lid is being welded.
FIG. 16(c) is a vertical sectional view of the injection needle unit in a state that the opening is enclosed by the lid, according to a tenth embodiment of the present invention.

Next, a tenth embodiment of the present invention will be explained with reference to FIG. 16. In the present embodiment, first, as illustrated in FIG. 16(a), the portion, in which the opening 137 of the needle base body 115 has been formed, is protruding. Next, as illustrated in FIG. 16(b), the protruding portion as described above is welded, for example by using the ultrasonic welding apparatus 201. Consequently, as illustrated in FIG. 16(c), the welded portion becomes the lid 117, whereby the opening 137 is enclosed.

For reference, the other structure is substantially the same as that of the fourth embodiment described above, and the same reference signs will be allotted to the same elements in the drawings, and the explain thereof will be omitted.

Accordingly, it is possible to achieve substantially the same effect as that of the fourth embodiment described above. Moreover, since it is not necessary to provide the lid 117 as a separate molded product, the manufacturing thereof is easy, and the assembling work can be simplified.

Figure 17:
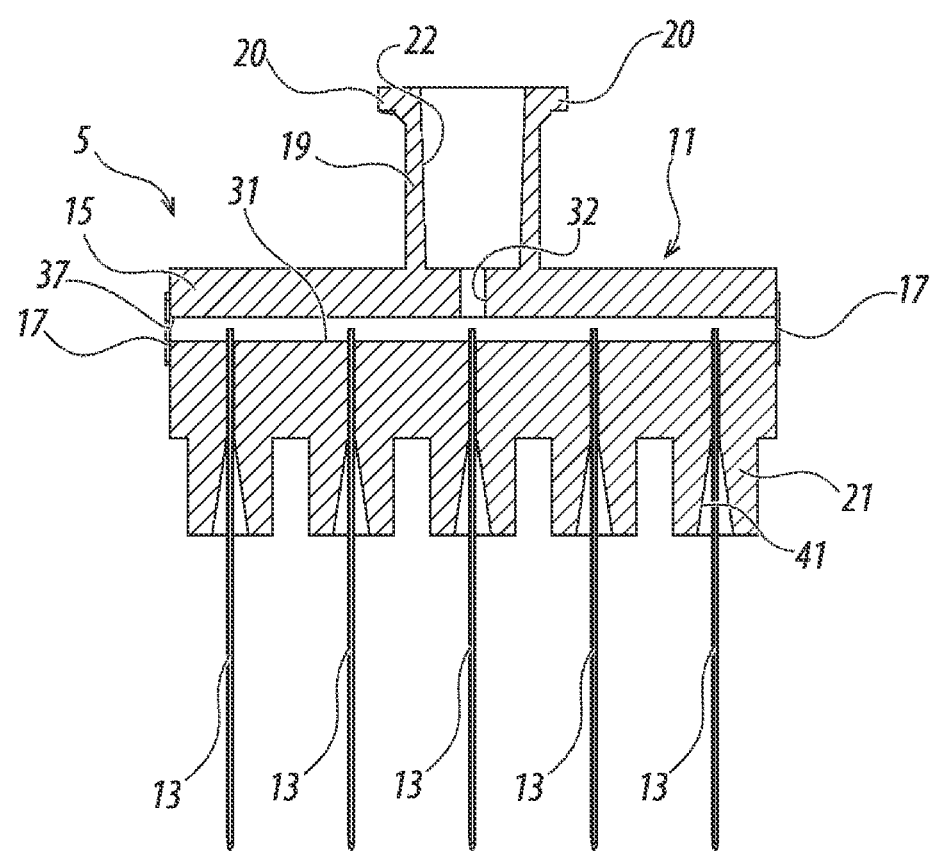
FIG. 17 is a vertical sectional view of an injection needle unit according to an eleventh embodiment of the present invention.

Next, an eleventh embodiment of the present invention will be explained with reference to FIG. 17. In the third embodiment as described above, the opening is provided on one side of the medicinal solution accommodation space 31, so as to be enclosed by the lid 17. However, in the eleventh embodiment, the openings are provided on the both sides, so as to be enclosed by the lids 17, 17.

For reference, the other structure is substantially the same as that of the third embodiment described above, and the same reference signs will be allotted to the same elements in the drawings, and the explain thereof will be omitted.

Accordingly, it is possible to insert the cores, which are used for molding of the medicinal solution accommodation space 31, from the openings on the both sides. Consequently, the thickness or the diameter of the core in itself can be reduced, whereby the size of the medicinal solution accommodation space 31 can be reduced, and eventually the dead space can be reduced further.

Figure 18:
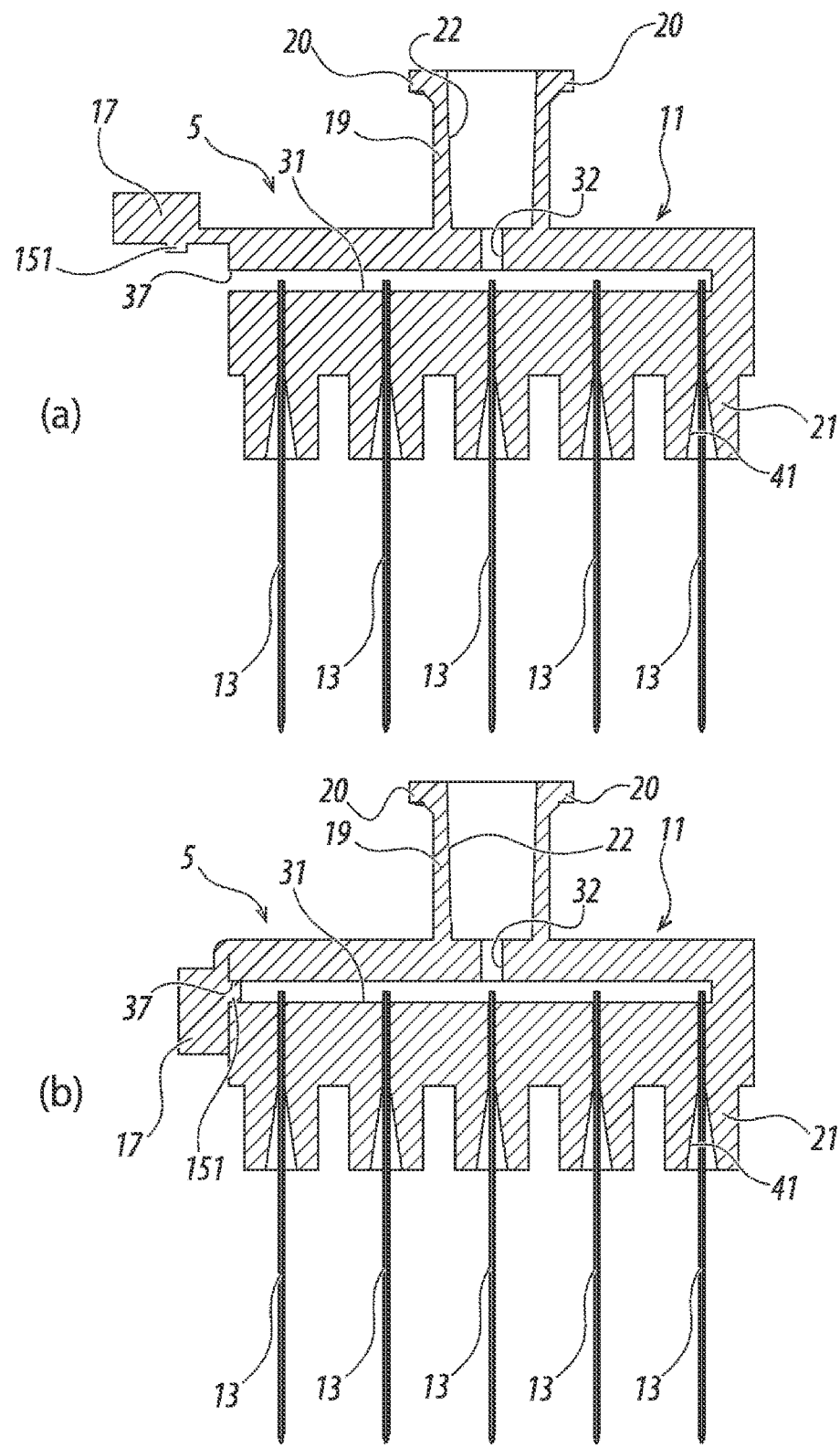
FIG. 18(a) is a vertical sectional view of an injection needle unit before an opening is enclosed by a lid.
FIG. 18(b) is a vertical sectional view of the injection needle unit in a state that the opening is enclosed by the lid, according to an twelfth embodiment of the present invention.

Next, a twelfth embodiment of the present invention will be explained with reference to FIG. 18. In the seventh embodiment as described above, the opening 37 is enclosed with the lid 17 being adhered or welded. However, in the twelfth embodiment, a projection 151 is provided on the lid 17, and the projection 151 is pressed to be fitted in the opening 37.

For reference, the other structure is substantially the same as that of the third embodiment described above, and the same reference signs will be allotted to the same elements in the drawings, and the explain thereof will be omitted.

Accordingly, it is possible to achieve substantially the same effect as that of the seventh embodiment described above.

Figure 19:
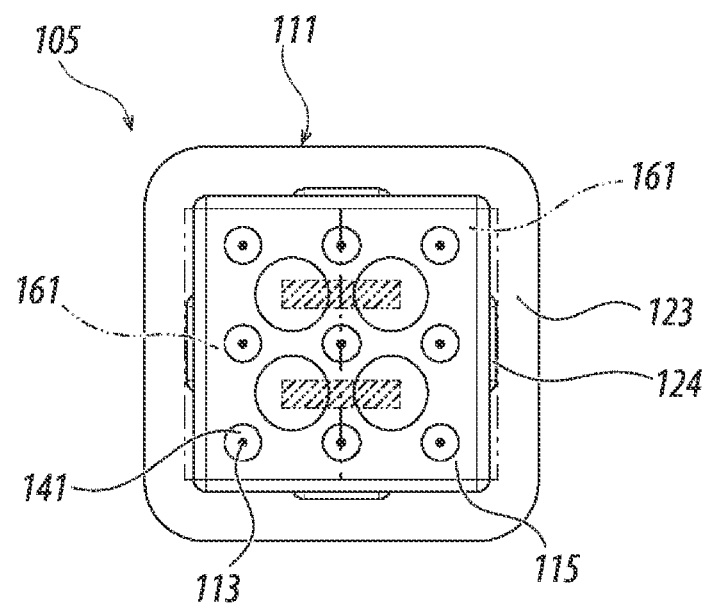
FIG. 19 is a bottom view of an injection needle unit according to an thirteenth embodiment of the present invention.

Next, a thirteenth embodiment of the present invention will be explained with reference to FIG. 19. With reference to the second embodiment, when the medicinal solution accommodation space 31 is formed, two cores 161, 161, as shown by imaginary lines in the drawing, may be used. The core 161 is in a shape of the letter "E," and during molding process, synthetic resin will intrude into the portions as shown by oblique lines in the drawing.

For reference, the other structure is substantially the same as that of the second embodiment described above, and the same reference signs will be allotted to the same elements in the drawings, and the explain thereof will be omitted.

Also in the present embodiment, it is possible to achieve substantially the same effect as that of the second embodiment, and the dead space can be reduced effectively.

The present invention is not limited to the first to the thirteenth embodiments as described above.

First, in the first to the thirteenth embodiments as described above, the needle base is composed of the needle base body and the lid. However, the present invention is not limited to those embodiments, and various two-component structure may be proposed. For example, it is possible to provide a structure in which two components are divided vertically.

Moreover, the first to the thirteenth embodiments are explained, as example purposes, with regard to the configuration of five rows in the longitudinal direction/a single row in the lateral direction, in total five needle pieces, and the configuration of three rows in the longitudinal direction/three rows in the lateral direction, in total nine needle pieces. However, the present invention is not limited to those examples, and the number and the configuration of the needle pieces can be set for various occasions.

Moreover, various shape and size can be designed for the needle base body and the lid.

Moreover, in the first to the thirteenth embodiments as described above, the oriented directions of the slant edge surfaces of the needle pieces are regularly arranged. However, the oriented directions can also be arranged irregularly.

Moreover, in the first to the thirteenth embodiments as described above, the number of the openings of the medicinal solution accommodation space is set to one or two. However, it is also possible to set the number to three or more.

Moreover, with the appropriate combination of the configuration of the needle pieces with the shape of the core, the reduction of dead space can be accomplished.

Moreover, in the seventh, the eighth and the twelfth embodiments, with the bending of the lid, which has been formed integrally, the opening is enclosed. However, it is also possible that, the lid has been provided integrally at an arbitral position of the needle base body, for example via a thin portion. Accordingly, with the cutting or tearing thereof, the adhering, welding or the press fitting of the lid in the opening can be performed.

Furthermore, the structures shown in the drawings are merely for example purposes only.

INDUSTRIAL APPLICABILITY

The present invention relates to the injection needle unit and the injection device, which are used, for example, for injection against the skin, and in particular, relates to those, provided with a plurality of needle pieces, and having a simple structure and capable of easy manufacturing. The present invention is suitable, for example, for the injection needle unit and the injection device used for cosmetic treatment and operation.

EXPLANATION OF REFERENCE NUMERALS AND SIGNS

1 Injection Needle Unit
11 Needle Base
13 Needle Piece
15 Needle Base Body
17 Lid
31 Medicinal Solution Accommodation Space
33 Recess
37 Opening

The invention claimed is:

1. An injection needle unit, comprising:
a needle base having a medicinal solution accommodation space; and
a plurality of needle pieces, each being attached to the needle base and having a base end communicating with the medicinal solution accommodation space,
wherein the needle base includes a needle base body in which the medicinal solution accommodation space is formed, a syringe connecting portion provided at the needle base body, a plurality of needle piece connection portions, to which the plurality of needle pieces is connected, provided at a side opposite to the syringe connecting portion, an opening in the needle base body configured to remove a slide mold, and the opening is adjacent to the medicinal solution accommodation space in a direction orthogonal to axis directions of the needle pieces, and a lid directly attached to the needle base body for closing the opening of the needle base body,
wherein a recess is in the needle base body, and the opening is at a bottom of the recess, and the recess is larger than the opening, and the lid comprises an enclosing projection to enclose the opening as the lid engages the recess, the enclosing projection is tapered and is at a tip side of the lid, and the lid is flush with the recess.

2. The injection needle unit according to claim 1, wherein the needle piece connecting portions include a plurality of needle piece attaching through holes, each needle piece attaching through hole having a tip portion where a diameter gradually enlarges toward a tip side.

3. The injection needle unit according to claim 1, wherein the needle base body further includes a non-opening recess at a side opposite to the recess having the opening.

4. The injection needle unit according to claim 1, wherein the needle base body and the lid are formed as one piece.

5. The injection needle unit according to claim 1, wherein the plurality of needle pieces is arranges to multiple rows in a longitudinal direction and multiple rows in a lateral direction.

6. The injection needle unit according to claim 5, wherein the needle pieces have slant edge surfaces, the slant edge surfaces of the needle pieces other than a center needle piece are oriented inwardly in a radial direction or outwardly in the radial direction.

7. The injection needle unit according to claim 1, wherein a tip of each of the plurality of needle pieces has a slant edge surface, and an oriented direction of each of the slant edge surface is irregularly arranged.

8. The injection needle unit according to claim 1, wherein the opening is provided at an axis position same as the medicinal solution accommodation space along the axis directions of the needles.

9. The injection needle unit according to claim 1, wherein the opening is along a direction where the plurality of needles is arranged side by side.

10. The injection needle unit according to claim 8, wherein
   the plurality of needles is arranged in one row, and
   the opening is provided along a direction where the plurality of needles is arranged in one row.

11. The injection needle unit according to claim 9, wherein the needle base with the lid attached thereto for closing the opening has a rectangular shape.

\* \* \* \* \*